(12) United States Patent
Carlsson et al.

(10) Patent No.: US 6,838,089 B1
(45) Date of Patent: Jan. 4, 2005

(54) ANTIGEN DELIVERY SYSTEM AND METHOD OF PRODUCTION

(75) Inventors: Hans Carlsson, Mölndal (SE); Anette Larsson, Olofstorp (SE); Erik Söderlind, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/308,435

(22) PCT Filed: Apr. 9, 1999

(86) PCT No.: PCT/SE99/00582

§ 371 (c)(1),
(2), (4) Date: May 19, 1999

(87) PCT Pub. No.: WO99/52550

PCT Pub. Date: Oct. 21, 1999

(51) Int. Cl.[7] ............................................. A61K 9/127
(52) U.S. Cl. ..................... 424/450; 424/423; 424/426; 424/448; 424/449; 424/499; 424/501; 424/486; 424/422; 424/234.1; 424/181.1; 435/392; 528/272; 264/4.6; 504/103; 436/518; 436/174; 436/524; 436/527; 436/528
(58) Field of Search ................................ 436/518, 174, 436/524, 527, 528; 435/274, 392; 528/272, 481, 482, 488; 264/406; 424/423, 426, 448, 234.1, 449, 181.1, 499, 501, 486, 422, 450, 301, 481, 468, 466, 472, 482; 504/450, 103

(56) References Cited

U.S. PATENT DOCUMENTS

| | | | |
|---|---|---|---|
| 4,038,139 A | * 7/1977 | Birch | ........................ 435/392 |
| 4,917,893 A | 4/1990 | Okada et al. | |
| 4,919,929 A | 4/1990 | Beck | |
| 4,954,298 A | 9/1990 | Yamamoto et al. | |
| 5,075,109 A | 12/1991 | Tice et al. | |
| 5,417,986 A | 5/1995 | Reid et al. | |
| 5,529,777 A | 6/1996 | Andrianov et al. | |
| 5,538,729 A | 7/1996 | Czinn et al. | |
| 5,591,433 A | 1/1997 | Michael et al. | |
| 5,622,649 A | 4/1997 | Hunter et al. | |
| 6,322,805 B1 | * 11/2001 | Kim et al. | .................. 424/426 |
| 6,322,810 B1 | * 11/2001 | Alkan-Onyuksel et al. | . 424/450 |
| 6,521,736 B2 | * 2/2003 | Watterson et al. | .......... 528/272 |
| 6,569,805 B1 | * 5/2003 | Krahmer et al. | ............ 504/103 |

FOREIGN PATENT DOCUMENTS

| | | |
|---|---|---|
| EP | 0766967 | 4/1997 |
| EP | 0591452 | 5/1998 |
| EP | 0724433 | 12/1998 |
| WO | 9511009 | 4/1995 |
| WO | 9511010 | 4/1995 |
| WO | 9636317 | 11/1996 |
| WO | 9828357 | 7/1998 |

OTHER PUBLICATIONS

Research in Immunology, vol. 149, 1998, J. L. Cleland, "Development of stable formulations for PLGA/PLA in microsphere vaccines", pp. 45–47.
Journal of Controlled Release, 54, (1998), pp 15–27, D. Lemoine and V. Preat, "Polymeric nanoparticles as delivery system for influenza virus glycoproteins".
Dev. Biol. Stand, vol. 92, 1998, R.K. Gupta et al., "Biodegradable Polymer Microspheres as Vaccine Adjuvants and Delivery Systems", pp 63–78.
Advanced Drug Delivery Reviews, 32, 91998), pp 225–246, D. T. O'Hagan, M. Singh, R. K. Gupta, "Poly(lactide-c-o-glycolide) Microparticles for the development of single-dose controlled-release vaccines".
Chemical Abstracts, vol. 124, No. 6, Feb. 5, 1996, (Columbus, Ohio, USA), Greenway, Terrence E., et al., "Enhancement of protective immune responses to Venezuelan equine encephalitis (VEE) virus with microencapsulaed vccine", p. 1, The Abstract No. 66330, vaccine 1995, 13 (15), 1411–1420.
Dialog File 155: Medline; 07045834 922 10497, Production of a conserved adhesin by the human gastroduodenal pathogen Helicobacter pylori; P. Doig, J.W. Austin, M. Kostrzynska, and T.J. Trust; Department of Biochemistry and Microbiology, University of Victoria, British Columbia, Canada., J. Bacteriol (U.S.), Apr. 1992, 174 (8), pp. 2539–47.

* cited by examiner

Primary Examiner—Lynette R. F. Smith
Assistant Examiner—Ginny Allen Portner
(74) Attorney, Agent, or Firm—White & Case LLP

(57) ABSTRACT

The present invention concerns polymer particle vaccine delivery systems in which a water insoluble protein antigen, e.g. a lipidated HpaA protein, is incorporated with particles comprising a polymer matrix. The present invention also concerns a method for incorporating such a water insoluble protein antigen with a polymer matrix in order to produce a polymer particle vaccine delivery system. In addition, the invention also provides a vaccine composition comprising the polymer particle delivery system. The vaccine can be used to treat and/or reduce the risk of for example Helicobacter infection.

65 Claims, 6 Drawing Sheets

20kv X 1,500        10 μm

15kv X 20,000  1 μm

SEQUENCE LISTING

<160> NUMBER OF SEQ ID NOS: 25

<210> SEQ ID NO 1
<211> LENGTH: 1670
<212> TYPE: DNA
<213> ORGANISM: Helicobacter pylori
<220> FEATURE:
<221> NAME/KEY: CDS
<222> LOCATION: (793)..(1572)

<400> SEQUENCE: 1

```
gatcctatcg cgccaaaggt ggtattagga ataagagctt gattattaat ctccctggta      60
agtccaaaaa gtattagaga atgcttagag gcggtttttc cagcgattcc ttattgcgtg     120
gatttgattt tagggaatta catgcaagtg aatgaaaaaa acattcaagc gtttgccccc     180
aaacaataag gtaaaaaatg ccactcactc atttgaatga agaaaatcaa cctaaaatgg     240
tggatatagg ggataaagaa accactgaaa gaatcgctct agcaagcggt cgtatcagca     300
tgaataaaga ggcttatgac gctattatca atcatggcgt caaaaagggt ccggtattac     360
aaactgctat tattgctggg attatggggg ctaaaaagac aagcgaactc attcccatgt     420
gccatccaat catgctcaat ggggtggata ttgatatttt agaagaaaaa gagacttgta     480
gttttaaact ctatgcgaga gtcaaaactc aagctaaaac gggcgtagaa atggaagcgc     540
taatgagtgt gagcgtaggg ctttta acca tttatgacat ggtgaaagcc attgataaga     600
gcatgacaat tagcggtgtg atgctggaat ataaagtgg aggcaaaagt ggggattata     660
acgctaaaaa atagaaaaag actgataatc taaagatatt agggtaaaat aacattttga     720
caacaaaagc gtgttggttg cttcggattt gttgttatag aagtctaaaa tattacaatc     780
aaggatagaa cg atg aga gca aat aat cat ttt aaa gat ttt gca tgg aaa    831
             Met Arg Ala Asn Asn His Phe Lys Asp Phe Ala Trp Lys
               1               5                  10 aaa tgc ctt tta ggc gcg agc gtg gtg gct tta tta gtg gga tgc agc       879
Lys Cys Leu Leu Gly Ala Ser Val Val Ala Leu Leu Val Gly Cys Ser
 15                  20                  25 ccg cat att att gaa acc aat gaa gtc gct ttg aaa ttg aat tac cat       927
Pro His Ile Ile Glu Thr Asn Glu Val Ala Leu Lys Leu Asn Tyr His
 30                  35                  40                  45 cca gct agc gag aaa gtt caa gcg tta gat gaa aag att ttg ctt tta       975
Pro Ala Ser Glu Lys Val Gln Ala Leu Asp Glu Lys Ile Leu Leu Leu
             50                  55                  60 agg cca gct ttc caa tat agc gat aat atc gct aaa gag tat gaa aac      1023
Arg Pro Ala Phe Gln Tyr Ser Asp Asn Ile Ala Lys Glu Tyr Glu Asn
         65                  70                  75 aaa ttc aag aat caa acc gcg ctc aag gtt gaa cag att ttg caa aat      1071
Lys Phe Lys Asn Gln Thr Ala Leu Lys Val Glu Gln Ile Leu Gln Asn
     80                  85                  90 caa ggc tat aag gtt att agc gta gat agc agc gat aaa gac gat ttt      1119
Gln Gly Tyr Lys Val Ile Ser Val Asp Ser Ser Asp Lys Asp Asp Phe
 95                 100                 105 tct ttt gca caa aaa aaa gaa ggg tat ttg gcg gtt gct atg aat ggc      1167
Ser Phe Ala Gln Lys Lys Glu Gly Tyr Leu Ala Val Ala Met Asn Gly
110                 115                 120                 125 gaa att gtt tta cgc ccc gat cct aaa agg acc ata cag aaa aaa tca      1215
Glu Ile Val Leu Arg Pro Asp Pro Lys Arg Thr Ile Gln Lys Lys Ser
             130                 135                 140 gaa ccc ggg tta tta ttc tcc acc ggt ttg gac aaa atg gaa ggg gtt      1263
Glu Pro Gly Leu Leu Phe Ser Thr Gly Leu Asp Lys Met Glu Gly Val
```

-continued

```
                    145                 150                 155
tta atc ccg gct ggg ttt att aag gtt acc ata cta gag cct atg agt       1311
Leu Ile Pro Ala Gly Phe Ile Lys Val Thr Ile Leu Glu Pro Met Ser
        160                 165                 170 ggg gaa tct ttg gat tct ttt acg atg gat ttg agc gag ttg gac att       1359
Gly Glu Ser Leu Asp Ser Phe Thr Met Asp Leu Ser Glu Leu Asp Ile
    175                 180                 185 caa gaa aaa ttc tta aaa acc acc cat tca agc cat agc ggg ggg tta       1407
Gln Glu Lys Phe Leu Lys Thr Thr His Ser Ser His Ser Gly Gly Leu
190                 195                 200                 205 gtt agc act atg gtt aag gga acg gat aat tct aat gac gcg atc aag       1455
Val Ser Thr Met Val Lys Gly Thr Asp Asn Ser Asn Asp Ala Ile Lys
                210                 215                 220 agc gct ttg aat aag att ttt gca aat atc atg caa gaa ata gac aaa       1503
Ser Ala Leu Asn Lys Ile Phe Ala Asn Ile Met Gln Glu Ile Asp Lys
            225                 230                 235 aaa ctc act caa aag aat tta gaa tct tat caa aaa gac gcc aaa gaa       1551
Lys Leu Thr Gln Lys Asn Leu Glu Ser Tyr Gln Lys Asp Ala Lys Glu
        240                 245                 250 tta aaa ggc aaa aga aac cga taaaaacaaa taacgcataa gaaaagaacg          1602
Leu Lys Gly Lys Arg Asn Arg
    255                 260 cttgaataaa ctgcttaaaa agggtttttt agcgttcttt ttgagcgtgt atttaagggc     1662
tgatgatc                                                              1670
```

<210> SEQ ID NO 2
<211> LENGTH: 260
<212> TYPE: PRT
<213> ORGANISM: Helicobacter pylori

<400> SEQUENCE: 2

```
Met Arg Ala Asn Asn His Phe Lys Asp Phe Ala Trp Lys Lys Cys Leu
  1               5                  10                  15

Leu Gly Ala Ser Val Val Ala Leu Leu Val Gly Cys Ser Pro His Ile
                 20                  25                  30

Ile Glu Thr Asn Glu Val Ala Leu Lys Leu Asn Tyr His Pro Ala Ser
             35                  40                  45

Glu Lys Val Gln Ala Leu Asp Glu Lys Ile Leu Leu Leu Arg Pro Ala
         50                  55                  60

Phe Gln Tyr Ser Asp Asn Ile Ala Lys Glu Tyr Glu Asn Lys Phe Lys
 65                  70                  75                  80

Asn Gln Thr Ala Leu Lys Val Glu Gln Ile Leu Gln Asn Gln Gly Tyr
                 85                  90                  95

Lys Val Ile Ser Val Asp Ser Ser Asp Lys Asp Phe Ser Phe Ala
            100                 105                 110

Gln Lys Lys Glu Gly Tyr Leu Ala Val Ala Met Asn Gly Glu Ile Val
        115                 120                 125

Leu Arg Pro Asp Pro Lys Arg Thr Ile Gln Lys Lys Ser Glu Pro Gly
    130                 135                 140

Leu Leu Phe Ser Thr Gly Leu Asp Lys Met Glu Gly Val Leu Ile Pro
145                 150                 155                 160

Ala Gly Phe Ile Lys Val Thr Ile Leu Glu Pro Met Ser Gly Glu Ser
                165                 170                 175

Leu Asp Ser Phe Thr Met Asp Leu Ser Glu Leu Asp Ile Gln Glu Lys
            180                 185                 190

Phe Leu Lys Thr Thr His Ser Ser His Ser Gly Gly Leu Val Ser Thr
```

```
                195                    200                    205
Met Val Lys Gly Thr Asp Asn Ser Asn Asp Ala Ile Lys Ser Ala Leu
        210                    215                    220

Asn Lys Ile Phe Ala Asn Ile Met Gln Glu Ile Asp Lys Lys Leu Thr
225                    230                    235                    240

Gln Lys Asn Leu Glu Ser Tyr Gln Lys Asp Ala Lys Glu Leu Lys Gly
                245                    250                    255

Lys Arg Asn Arg
            260

<210> SEQ ID NO 3
<211> LENGTH: 1670
<212> TYPE: DNA
<213> ORGANISM: Helicobacter pylori
<220> FEATURE:
<221> NAME/KEY: CDS
<222> LOCATION: (793)..(1572)

<400> SEQUENCE: 3
gatcctatcg cgccaaaggt ggtattagga ataagagctt gattattaat ctccctggta      60
agtccaaaaa gtattagaga atgcttagag gcggtttttc cagcgattcc ttattgcgtg     120
gatttgattt tagggaatta catgcaagtg aatgaaaaaa acattcaagc gtttgcccccc     180 aaacaataag gtaaaaaatg ccactcactc atttgaatga agaaaatcaa cctaaaatgg     240
tggatatagg ggataaagaa accactgaaa gaatcgctct agcaagcggt cgtatcagca     300
tgaataaaga ggcttatgac gctattatca atcatggcgt caaaaagggt ccggtattac     360
aaactgctat tattgctggg attatggggg ctaaaaagac aagcgaactc attcccatgt     420
gccatccaat catgctcaat ggggtggata ttgatatttt agaagaaaaa gagacttgta     480
gttttaaact ctatgcgaga gtcaaaactc aagctaaaac gggcgtagaa atggaagcgc     540
taatgagtgt gagcgtaggg cttttaacca tttatgacat ggtgaaagcc attgataaga     600
gcatgacaat tagcggtgtg atgctggaat ataaaagtgg aggcaaaagt ggggattata     660
acgctaaaaa atagaaaaag actgataatc taaagatatt agggtaaaat aacattttga     720
caacaaaagc gtgttggttg cttcggattt gttgttatag aagtctaaaa tattacaatc     780
aaggatagaa cg atg aga gca aat aat cat ttt aaa gat ttt gca tgg aaa     831
          Met Arg Ala Asn Asn His Phe Lys Asp Phe Ala Trp Lys
              1               5                   10 aaa tgc ctt tta ggc gcg agc gtg gtg gct tta tta gtg gga tgc agc       879
Lys Cys Leu Leu Gly Ala Ser Val Val Ala Leu Leu Val Gly Cys Ser
 15                  20                  25 ccg cat att att gaa acc aat gaa gtc gct ttg aaa ttg aat tac cat       927
Pro His Ile Ile Glu Thr Asn Glu Val Ala Leu Lys Leu Asn Tyr His
 30                  35                  40                  45 cca gct agc gag aaa gtt caa gcg tta gat gaa aag att ttg ctt tta       975
Pro Ala Ser Glu Lys Val Gln Ala Leu Asp Glu Lys Ile Leu Leu Leu
                 50                  55                  60 agg cca gct ttc caa tat agc gat aat atc gct aaa gag tat gaa aac      1023
Arg Pro Ala Phe Gln Tyr Ser Asp Asn Ile Ala Lys Glu Tyr Glu Asn
             65                  70                  75 aaa ttc aag aat caa acc gcg ctc aag gtt gaa cag att ttg caa aat      1071
Lys Phe Lys Asn Gln Thr Ala Leu Lys Val Glu Gln Ile Leu Gln Asn
         80                  85                  90 caa ggc tat aag gtt att agc gta gat agc agc gat aaa gac gat ttt      1119
Gln Gly Tyr Lys Val Ile Ser Val Asp Ser Ser Asp Lys Asp Asp Phe
     95                 100                 105
```

```
tct ttt gca caa aaa aaa gaa ggg tat ttg gcg gtt gct atg aat ggc    1167
Ser Phe Ala Gln Lys Lys Glu Gly Tyr Leu Ala Val Ala Met Asn Gly
110                 115                 120                 125 gaa att gtt tta cgc ccc gat cct aaa agg acc ata cag aaa aaa tca    1215
Glu Ile Val Leu Arg Pro Asp Pro Lys Arg Thr Ile Gln Lys Lys Ser
            130                 135                 140 gaa ccc ggg tta tta ttc tcc acc ggt ttg gac aaa atg gaa ggg gtt    1263
Glu Pro Gly Leu Leu Phe Ser Thr Gly Leu Asp Lys Met Glu Gly Val
        145                 150                 155 tta atc ccg gct ggg ttt att aag gtt acc ata cta gag cct atg agt    1311
Leu Ile Pro Ala Gly Phe Ile Lys Val Thr Ile Leu Glu Pro Met Ser
    160                 165                 170 ggg gaa tct ttg gat tct ttt acg atg gat ttg agc gag ttg gac att    1359
Gly Glu Ser Leu Asp Ser Phe Thr Met Asp Leu Ser Glu Leu Asp Ile
175                 180                 185 caa gaa aaa ttc tta aaa acc acc cat tca agc cat agc ggg ggg tta    1407
Gln Glu Lys Phe Leu Lys Thr Thr His Ser Ser His Ser Gly Gly Leu
190                 195                 200                 205 gtt agc act atg gtt aag gga acg gat aat tct aat gac gcg atc aag    1455
Val Ser Thr Met Val Lys Gly Thr Asp Asn Ser Asn Asp Ala Ile Lys
            210                 215                 220 aga gct ttg aat aag att ttt gca aat atc atg caa gaa ata gac aaa    1503
Arg Ala Leu Asn Lys Ile Phe Ala Asn Ile Met Gln Glu Ile Asp Lys
        225                 230                 235 aaa ctc act caa aag aat tta gaa tct tat caa aaa gac gcc aaa gaa    1551
Lys Leu Thr Gln Lys Asn Leu Glu Ser Tyr Gln Lys Asp Ala Lys Glu
    240                 245                 250 tta aaa ggc aaa aga aac cga taaaaacaaa taacgcataa gaaaagaacg       1602
Leu Lys Gly Lys Arg Asn Arg
255                 260 cttgaataaa ctgcttaaaa agggtttttt agcgttcttt ttgagcgtgt atttaagggc  1662
tgatgatc                                                           1670
```

<210> SEQ ID NO 4
<211> LENGTH: 260
<212> TYPE: PRT
<213> ORGANISM: Helicobacter pylori

<400> SEQUENCE: 4

```
Met Arg Ala Asn Asn His Phe Lys Asp Phe Ala Trp Lys Lys Cys Leu
 1               5                  10                  15

Leu Gly Ala Ser Val Val Ala Leu Leu Val Gly Cys Ser Pro His Ile
            20                  25                  30

Ile Glu Thr Asn Glu Val Ala Leu Lys Leu Asn Tyr His Pro Ala Ser
        35                  40                  45

Glu Lys Val Gln Ala Leu Asp Glu Lys Ile Leu Leu Leu Arg Pro Ala
    50                  55                  60

Phe Gln Tyr Ser Asp Asn Ile Ala Lys Glu Tyr Glu Asn Lys Phe Lys
65                  70                  75                  80

Asn Gln Thr Ala Leu Lys Val Glu Gln Ile Leu Gln Asn Gln Gly Tyr
                85                  90                  95

Lys Val Ile Ser Val Asp Ser Ser Asp Lys Asp Asp Phe Ser Phe Ala
            100                 105                 110

Gln Lys Lys Glu Gly Tyr Leu Ala Val Ala Met Asn Gly Glu Ile Val
        115                 120                 125

Leu Arg Pro Asp Pro Lys Arg Thr Ile Gln Lys Lys Ser Glu Pro Gly
    130                 135                 140
```

-continued

```
Leu Leu Phe Ser Thr Gly Leu Asp Lys Met Glu Gly Val Leu Ile Pro
145                 150                 155                 160

Ala Gly Phe Ile Lys Val Thr Ile Leu Glu Pro Met Ser Gly Glu Ser
                165                 170                 175

Leu Asp Ser Phe Thr Met Asp Leu Ser Glu Leu Asp Ile Gln Glu Lys
            180                 185                 190

Phe Leu Lys Thr Thr His Ser Ser His Ser Gly Gly Leu Val Ser Thr
        195                 200                 205

Met Val Lys Gly Thr Asp Asn Ser Asn Asp Ala Ile Lys Arg Ala Leu
    210                 215                 220

Asn Lys Ile Phe Ala Asn Ile Met Gln Glu Ile Asp Lys Lys Leu Thr
225                 230                 235                 240

Gln Lys Asn Leu Glu Ser Tyr Gln Lys Asp Ala Lys Glu Leu Lys Gly
                245                 250                 255

Lys Arg Asn Arg
            260

<210> SEQ ID NO 5
<211> LENGTH: 60
<212> TYPE: PRT
<213> ORGANISM: Helicobacter pylori

<400> SEQUENCE: 5

Met Lys Thr Asn Gly His Phe Lys Asp Phe Ala Trp Lys Lys Cys Leu
 1               5                  10                  15

Leu Gly Thr Ser Val Val Ala Leu Leu Val Gly Cys Ser Pro His Ile
            20                  25                  30

Ile Glu Thr Asn Glu Val Ala Leu Lys Leu Asn Tyr His Pro Ala Ser
        35                  40                  45

Glu Lys Val Gln Ala Leu Asp Glu Lys Ile Leu Leu
    50                  55                  60

<210> SEQ ID NO 6
<211> LENGTH: 60
<212> TYPE: PRT
<213> ORGANISM: Helicobacter pylori

<400> SEQUENCE: 6

Met Lys Thr Asn Gly His Phe Lys Asp Phe Ala Trp Lys Lys Cys Phe
 1               5                  10                  15

Leu Gly Ala Ser Val Val Ala Leu Leu Val Gly Cys Ser Pro His Ile
            20                  25                  30

Ile Glu Thr Asn Glu Val Ala Leu Lys Leu Asn Tyr His Pro Ala Ser
        35                  40                  45

Glu Lys Val Gln Ala Leu Asp Glu Lys Ile Leu Leu
    50                  55                  60

<210> SEQ ID NO 7
<211> LENGTH: 60
<212> TYPE: PRT
<213> ORGANISM: Helicobacter pylori

<400> SEQUENCE: 7

Met Lys Thr Asn Gly His Phe Lys Asp Phe Ala Trp Lys Lys Cys Leu
 1               5                  10                  15

Leu Gly Ala Ser Val Gly Ala Leu Leu Val Gly Cys Ser Pro His Ile
            20                  25                  30

Ile Glu Thr Asn Glu Val Ala Leu Lys Leu Asn Tyr His Pro Ala Ser
```

```
                35                  40                  45
Glu Lys Val Gln Ala Leu Asp Glu Lys Ile Leu Leu
    50                  55                  60

<210> SEQ ID NO 8
<211> LENGTH: 60
<212> TYPE: PRT
<213> ORGANISM: Helicobacter pylori

<400> SEQUENCE: 8

Met Arg Ala Asn Asn His Phe Lys Asp Phe Ala Trp Lys Lys Cys Leu
 1               5                  10                  15

Leu Gly Ala Ser Val Val Ala Leu Leu Val Gly Cys Ser Pro His Ile
                20                  25                  30

Ile Glu Thr Asn Glu Val Ala Leu Lys Leu Asn Tyr His Pro Ala Ser
            35                  40                  45

Glu Lys Val Gln Ala Leu Asp Glu Lys Ile Leu Leu
    50                  55                  60

<210> SEQ ID NO 9
<211> LENGTH: 60
<212> TYPE: PRT
<213> ORGANISM: Helicobacter pylori

<400> SEQUENCE: 9

Met Lys Ala Asn Asn His Phe Lys Asp Phe Ala Trp Lys Lys Cys Leu
 1               5                  10                  15

Leu Gly Ala Ser Val Val Ala Leu Leu Val Gly Cys Ser Pro His Ile
                20                  25                  30

Ile Glu Thr Asn Glu Val Ala Leu Lys Leu Asn Tyr His Pro Ala Ser
            35                  40                  45

Glu Lys Val Gln Ala Leu Asp Glu Lys Ile Leu Leu
    50                  55                  60

<210> SEQ ID NO 10
<211> LENGTH: 60
<212> TYPE: PRT
<213> ORGANISM: Helicobacter pylori

<400> SEQUENCE: 10

Leu Lys Pro Ala Phe Gln Tyr Ser Asp Asn Ile Ala Lys Glu Tyr Glu
 1               5                  10                  15

Asn Lys Phe Lys Asn Gln Thr Thr Leu Lys Val Glu Glu Ile Leu Gln
                20                  25                  30

Asn Gln Gly Tyr Lys Val Ile Asn Val Asp Ser Ser Asp Lys Asp Asp
            35                  40                  45

Phe Ser Phe Ala Gln Lys Lys Glu Gly Tyr Leu Ala
    50                  55                  60

<210> SEQ ID NO 11
<211> LENGTH: 60
<212> TYPE: PRT
<213> ORGANISM: Helicobacter pylori

<400> SEQUENCE: 11

Leu Arg Pro Ala Phe Gln Tyr Ser Asp Asn Ile Ala Lys Glu Tyr Glu
 1               5                  10                  15

Asn Lys Phe Lys Asn Gln Thr Thr Leu Lys Val Glu Glu Ile Leu Gln
                20                  25                  30
```

Asn Gln Gly Tyr Lys Val Ile Asn Val Asp Ser Ser Asp Lys Asp Asp
            35                  40                  45

Phe Ser Phe Ala Gln Lys Lys Glu Gly Tyr Leu Ala
        50                  55                  60

<210> SEQ ID NO 12
<211> LENGTH: 60
<212> TYPE: PRT
<213> ORGANISM: Helicobacter pylori

<400> SEQUENCE: 12

Leu Arg Pro Ala Phe Gln Tyr Ser Asp Asn Ile Ala Lys Glu Tyr Glu
  1               5                  10                  15

Asn Lys Phe Lys Asn Gln Thr Val Leu Lys Val Glu Gln Ile Leu Gln
            20                  25                  30

Asn Gln Gly Tyr Lys Val Ile Asn Val Asp Ser Ser Asp Lys Asp Asp
            35                  40                  45

Phe Ser Phe Ala Gln Lys Lys Glu Gly Tyr Leu Ala
        50                  55                  60

<210> SEQ ID NO 13
<211> LENGTH: 60
<212> TYPE: PRT
<213> ORGANISM: Helicobacter pylori

<400> SEQUENCE: 13

Leu Arg Pro Ala Phe Gln Tyr Ser Asp Asn Ile Ala Lys Glu Tyr Glu
  1               5                  10                  15

Asn Lys Phe Lys Asn Gln Thr Ala Leu Lys Val Glu Gln Ile Leu Gln
            20                  25                  30

Asn Gln Gly Tyr Lys Val Ile Ser Val Asp Ser Ser Asp Lys Asp Asp
            35                  40                  45

Phe Ser Phe Ala Gln Lys Lys Glu Gly Tyr Leu Ala
        50                  55                  60

<210> SEQ ID NO 14
<211> LENGTH: 60
<212> TYPE: PRT
<213> ORGANISM: Helicobacter pylori

<400> SEQUENCE: 14

Leu Arg Pro Ala Phe Gln Tyr Ser Asp Asn Ile Ala Lys Glu Tyr Glu
  1               5                  10                  15

Asn Lys Phe Lys Asn Gln Thr Ala Leu Lys Val Glu Gln Ile Leu Gln
            20                  25                  30

Asn Gln Gly Tyr Lys Val Ile Ser Val Asp Ser Ser Asp Lys Asp Asp
            35                  40                  45

Leu Ser Phe Ser Gln Lys Lys Glu Gly Tyr Leu Ala
        50                  55                  60

<210> SEQ ID NO 15
<211> LENGTH: 60
<212> TYPE: PRT
<213> ORGANISM: Helicobacter pylori

<400> SEQUENCE: 15

Val Ala Met Ile Gly Glu Ile Val Leu Arg Pro Asp Pro Lys Arg Thr
  1               5                  10                  15

Ile Gln Lys Lys Ser Glu Pro Gly Leu Leu Phe Ser Thr Gly Leu Asp
            20                  25                  30

```
Lys Met Glu Gly Val Leu Ile Pro Ala Gly Phe Val Lys Val Thr Ile
            35                  40                  45

Leu Glu Pro Met Ser Gly Glu Ser Leu Asp Ser Phe
        50                  55                  60

<210> SEQ ID NO 16
<211> LENGTH: 60
<212> TYPE: PRT
<213> ORGANISM: Helicobacter pylori

<400> SEQUENCE: 16

Val Ala Met Asn Gly Glu Ile Val Leu Arg Pro Asp Pro Lys Arg Thr
 1               5                  10                  15

Ile Gln Lys Lys Ser Glu Pro Gly Leu Leu Phe Ser Thr Gly Leu Asp
            20                  25                  30

Lys Met Glu Gly Val Leu Ile Pro Ala Gly Phe Val Lys Val Thr Ile
            35                  40                  45

Leu Glu Pro Met Ser Gly Glu Ser Leu Asp Ser Phe
        50                  55                  60

<210> SEQ ID NO 17
<211> LENGTH: 60
<212> TYPE: PRT
<213> ORGANISM: Helicobacter pylori

<400> SEQUENCE: 17

Val Ala Met Asn Gly Glu Ile Val Leu Arg Pro Asp Pro Lys Arg Thr
 1               5                  10                  15

Ile Gln Lys Lys Ser Glu Pro Gly Leu Leu Phe Ser Thr Gly Leu Asp
            20                  25                  30

Lys Met Glu Gly Val Leu Ile Pro Ala Gly Phe Ile Lys Val Thr Ile
            35                  40                  45

Leu Glu Pro Met Ser Gly Glu Ser Leu Asp Ser Phe
        50                  55                  60

<210> SEQ ID NO 18
<211> LENGTH: 60
<212> TYPE: PRT
<213> ORGANISM: Helicobacter pylori

<400> SEQUENCE: 18

Thr Met Asp Leu Ser Glu Leu Asp Ile Gln Glu Lys Phe Leu Lys Thr
 1               5                  10                  15

Thr His Ser Ser His Ser Gly Gly Leu Val Ser Thr Met Val Lys Gly
            20                  25                  30

Thr Asp Asn Ser Asn Asp Ala Ile Lys Ser Ala Leu Asn Lys Ile Phe
            35                  40                  45

Ala Ser Ile Met Gln Glu Met Asp Lys Lys Leu Thr
        50                  55                  60

<210> SEQ ID NO 19
<211> LENGTH: 60
<212> TYPE: PRT
<213> ORGANISM: Helicobacter pylori

<400> SEQUENCE: 19

Thr Met Asp Leu Ser Glu Leu Asp Ile Gln Glu Lys Phe Leu Lys Thr
 1               5                  10                  15

Thr His Ser Ser His Ser Gly Gly Leu Val Ser Thr Met Val Lys Gly
```

```
                    20                  25                  30

Thr Asp Asn Ser Asn Asp Ala Ile Lys Ser Ala Leu Asn Lys Ile Phe
         35                  40                  45

Gly Ser Ile Met Gln Glu Ile Asp Lys Lys Leu Thr
     50                  55                  60

<210> SEQ ID NO 20
<211> LENGTH: 60
<212> TYPE: PRT
<213> ORGANISM: Helicobacter pylori

<400> SEQUENCE: 20

Thr Met Asp Leu Ser Glu Leu Asp Ile Gln Glu Lys Phe Leu Lys Thr
 1               5                  10                  15

Thr His Ser Ser His Ser Gly Gly Leu Val Ser Thr Met Val Lys Gly
                20                  25                  30

Thr Asp Asn Ser Asn Asp Ala Ile Lys Ser Ala Leu Asn Lys Ile Phe
         35                  40                  45

Ala Asn Ile Met Gln Glu Ile Asp Lys Lys Leu Thr
     50                  55                  60

<210> SEQ ID NO 21
<211> LENGTH: 20
<212> TYPE: PRT
<213> ORGANISM: Helicobacter pylori

<400> SEQUENCE: 21

Gln Arg Asn Leu Glu Ser Tyr Gln Lys Asp Ala Lys Glu Leu Lys Asn
 1               5                  10                  15

Lys Arg Asn Arg
            20

<210> SEQ ID NO 22
<211> LENGTH: 20
<212> TYPE: PRT
<213> ORGANISM: Helicobacter pylori

<400> SEQUENCE: 22

Gln Lys Asn Leu Glu Ser Tyr Gln Lys Asp Ala Lys Glu Leu Lys Gly
 1               5                  10                  15

Lys Arg Asn Arg
            20

<210> SEQ ID NO 23
<211> LENGTH: 31
<212> TYPE: PRT
<213> ORGANISM: Helicobacter pylori

<400> SEQUENCE: 23

Met Arg Ala Asn Asn His Phe Lys Asp Phe Ala Trp Lys Lys Cys Leu
 1               5                  10                  15

Leu Gly Ala Ser Val Val Ala Leu Leu Val Gly Leu Ala Gly Cys
                20                  25                  30

<210> SEQ ID NO 24
<211> LENGTH: 31
<212> TYPE: PRT
<213> ORGANISM: Helicobacter pylori
<220> FEATURE:
<221> NAME/KEY: MOD_RES
<222> LOCATION: (31)
<223> OTHER INFORMATION: n-propyl alcohol attached to sulfhydryl group
```

-continued of cysteine residue at position 31

<400> SEQUENCE: 24

Met Arg Ala Asn Asn His Phe Lys Asp Phe Ala Trp Lys Lys Cys Leu
 1               5                  10                  15

Leu Gly Ala Ser Val Val Ala Leu Leu Val Gly Leu Ala Gly Cys
            20                  25                  30

<210> SEQ ID NO 25
<211> LENGTH: 31
<212> TYPE: PRT
<213> ORGANISM: Helicobacter pylori
<220> FEATURE:
<221> NAME/KEY: MOD_RES
<222> LOCATION: (31)
<223> OTHER INFORMATION: lipid chains a and b attached respectively at
      positions 3  and 2  of propyl group attached to
      sulfhydryl of cysteine residue at position 31

<400> SEQUENCE: 25

Met Arg Ala Asn Asn His Phe Lys Asp Phe Ala Trp Lys Lys Cys Leu
 1               5                  10                  15

Leu Gly Ala Ser Val Val Ala Leu Leu Val Gly Leu Ala Gly Cys
            20                  25                  30

ANTIGEN DELIVERY SYSTEM AND METHOD OF PRODUCTION

FIELD OF THE INVENTION

The present invention concerns polymer particle vaccine delivery systems in which a water insoluble protein antigen is incorporated with particles comprising a polymer matrix. The present invention also concerns a method for incorporating such a water insoluble protein antigen with a polymer matrix in order to produce a polymer particle vaccine delivery system. In addition, the invention also provides a vaccine composition comprising the to polymer particle delivery system. The vaccine can be used to treat and/or reduce the risk of for example Helicobacter infection.

BACKGROUND TO THE INVENTION

Several different types of vaccine delivery systems have been described in the literature (see e g "Vaccine Design. The subunit and adjuvant approach" (Eds: M F Powell and M J Newman), Pharmaceutical Biotechnology, vol 6, Plenum Press, NY 1995). Examples of known delivery systems for vaccines include liposomes, cochleates and polymer particles of a biodegradable or non-biodegradable nature. Antigens have also been associated with live attenuated bacteria, viruses or phages or with killed vectors of the same kind.

Polymer particles are well suited as vaccine delivery systems, because they can be produced in a range of sizes (eg, microparticles and nanoparticles) according, for example, to the preferred administration route for the vaccine and can slowly release the antigen inside the patient in order to build up a desirable immune response of the patient without the need for multiple vaccinations. The antigen is incorporated with the particles by encapsulation within a matrix of the polymer, with or without adsorption of the antigen onto the surface of the polymer particles.

When the antigen is a protein, care must be taken to chose a preparation method for the polymer particles that does not remove the desired immunogenicity of the protein (eg, by denaturation). Thus, although various techniques are known for generally producing polymer particles with an active drug or substance, as explained below not all of these are well suited to use with a protein antigen.

The following general techniques have been used for preparing polymer particles:
1. Hot Melt Microencapsulation (A. J. Schwope et al *Life Sci*. 1975, 17,1877);
2. Interfacial Polymerisation (G. Birrenbach & P. Speiser, *J. Pharm.Sci*. 1976, 65, 1763, Thies, In Encyclopaedia of Chemical Technology, 4 ed., Ed. Kirk-Othmer, 1996, 16, p. 632);
3. Double Emulsion Solvent Evaporation Technique ("Vaccine Design. The subunit and adjuvant approach" (Eds: M F Powell and M J Newman), Pharmaceutical Biotechnology, vol 6, Plenum Press, NY 1995);
4. Double Emulsion Solvent Extraction Technique ("Vaccine Design. The subunit and adjuvant approach" (Eds: M F Powell and M J Newman), Pharmaceutical Biotechnology, vol 6, Plenum Press, NY 1995); and
5. Spray Drying (J. Cox, et al. WO 94/15636).

In the Hot Melt Microencapsulation method the matrix polymer is melted by heating while mixed with the active substance to incorporated with the particles. This technique is not well suited to use with a proteinaceous active substance, such as protein antigen, since the heating step tends to denature the active substance.

Interfacial Polymerisation is performed in following manner. A core material and the active substance are dissolved in a water immiscible solvent, together with a highly reactive monomer. This solution is then emulsified in water, where another monomer is dissolved, and a stable O/W emulsion is formed. An initiator is added to the water phase and polymerisation occurs, thereby forming a polymer particle incorporating the active substance. When the active substance is proteinaceous, the highly reactive monomer in the water immiscible solvent tends to react undesirably with the active substance as well as the core material, which means that Interfacial Polymerisation is not well suited to the incorporation of a protein antigen with polymer particles.

Techniques are available which entail the formation of a water-in-oil (W/O) emulsion in which the active substance is dissolved in the W phase can be used to incorporate a proteinaceous active substance with polymer particles. Examples are the Double Emulsion Solvent Extraction and Evaporation Techniques and the Spray Drying.

For incorporation of a protein using the Double Emulsion (W/O/X) Solvent Evaporation Technique, a multiple W/O/X emulsion is used. The first step is the formation of a first (W/O) emulsion, in which the protein is dissolved in a first aqueous phase (W) and the oil (O) phase contains the matrix polymer and an organic solvent, the W and O phases being emulsified for example by ultra-sonication. In a second step, this first emulsion is then emulsified in a third phase (X) to form multiple W/O emulsion droplets dispersed in the X is phase, which is commonly a second aqueous phase, but may for example be oil (eg sesame oil) instead. The organic solvent diffuses out from the droplets into the X phase before evaporating from the X phase. Thus, the organic solvent moves from the oil phase of the W/O emulsion droplets, to the X phase and then to the air. This results in a decrease of the organic solvent concentration in the O phase, and opposite an increase in the polymer concentration, since the polymer does not move with the organic solvent to the X phase. At a certain polymer concentration the polymer precipitates, thereby producing polymer particles comprising a matrix of the polymer incorporated with the protein (ie, protein is encapsulated within the matrix with or without surface adsorption onto the outside of the particle).

The Double Emulsion (W/O/X) Solvent Extraction Technique is similar to the Double Emulsion Solvent Evaporation Technique, but the organic solvent is extracted from the O phase of the W/O emulsion instead of being removed by evaporation. In addition, a second oil phase is used as the X phase in the double emulsion. The second oil phase extracts the organic solvent from the O phase, thereby raising the matrix polymer concentration in the O phase and leading to polymer particle formation in which the protein is incorporated with the particles. (Lewis, *Drugs and the Pharmaceutical Sciences* (M Chasin and R Langer, eds.), Vol. 45, Dekker, New York, 1990, pp 1–42).

In the Spray Drying Technique, a W/O emulsion is formed as discussed above. The emulsion is sprayed through a nozzle to produce small droplets of the emulsion (dispersed in air) from which the solvent rapidly evaporates, thereby leading to formation of polymer particles incorporated with the protein. Microparticles in the 1–10 $\mu$m size range can be prepared (at relatively low cost) with this technique.

Biodegradable polymer particles are particularly well suited for use as vaccine delivery systems, because the polymer matrix itself is non-immunogenic and the encapsulation of the antigen protects it from degradation in the gastrointestinal tract (eg, by acid and proteases). An example of an especially suitable matrix polymer is PLG (poly (lactide-co-glycolide) copolymers—also known as PLGA and PLA). PLG particles have excellent tissue biocompatibility, biodegradability and regulatory approval. PLG particles degrade in vivo to form the non-toxic monomers, lactic- and glycolic acids and the release rate of incorporated active substances can be controlled by varying the molecular weight and copolymer ratio.

Examples of documents disclosing the use of Double Emulsion Techniques for incorporating water soluble proteins or peptides with PLG particles include:

H Rafati et al, "Protein-loaded poly(DL-lactide-coglycolide) microparticles for oral administration: formulation, structural and release characteristics", J. Controlled Release 43 (1997), pp 89–102. This article discloses the use of a Double Emulsion (W1/O/W2) Solvent Evaporation Technique for incorporating bovine serum albumin (BSA) with particles of PLG.

M J Blanco-Prieto et al, "Characterization and morphological analysis of a cholecystokinin derivative peptide-loaded poly(lactide-co-glycolide) microspheres prepared by a water-in-oil-in-water emulsion solvent evaporation method", J. Controlled Release 43 (1997), pp 81–87. This article discloses the incorporation of a small water soluble peptide with PLG particles. The authors observe that the stabilisation of the inner emulsion in the double emulsion by the combined use of OVA (ovalbumin) together with the use of a pH gradient between the inner and outer aqueous phase improved peptide encapsulation.

R V Diaz et al, "Effect of surfactant agents on the release of $^{125}$I-bovine calcitonin from PLGA microspheres: in vitro—in vivo study", J. Controlled Release 43 (1997), pp 59–64. This article aims to investigate the possible influence that the surfactants Tween®-80 and Span®-60 (included in the W1 and O phases respectively) could have on the in vitro and in vivo release profile of $^{125}$I-bovine calcitonin from PLGA microspheres. The article concludes that the protein encapsulation efficiency is similar independent of the presence or absence of the surfactants.

The prior art has therefore only concerned the incorporation of water soluble proteins and peptides with polymer particles using techniques which involve the formation of a W/O emulsion. The reason for this is that for the desired protein incorporation to take place, the protein must be solubilised in the W aqueous phase in order eventually to produce droplets of W/O emulsion in which the aqueous phase containing the solubilised protein provides the core of the droplets surrounded by the O phase which contains the matrix polymer in an organic solvent.

These techniques have not previously been considered to be useable for the incorporation of water insoluble proteins, because it was thought that these proteins cannot be suitably solubilised in the aqueous W phase.

Note that protein denaturation (eg, unfolding) by the organic solvent precludes the provision of the protein in an O phase together with the matrix polymer in order to produce polymer particles incorporated with a protein antigen. WO 95/11009, WO 95/11010, WO 96/36317, U.S. Pat. No. 5,075,109, U.S. Pat. No. 4,919,929 and U.S. Pat. No. 5,529,777 disclose the formation of microparticles incorporating water soluble antigens. None of these documents discloses the incorporation of a water insoluble protein antigen into polymer particles: WO 95/11009 and WO 95/11010 disclose the microencapsulation of MN rpg120 or QS21 into PLGA; WO 96/36317 discloses the formation of microparticles comprising a polymer matrix (eg, PLG) and a biological agent, further agents being optionally included in order to maintain the potency of the biological agent over the duration of the biological agent's release from the microparticles and to modify the release rate of the biological agent from the microparticles; U.S. Pat. No. 5,075,109 discloses the formation of microparticles incorporating trinitrophenyl keyhole limpet hemocyanin or staphylococcal enterotoxin B as an antigen; and U.S. Pat. No. 5,529,777 discloses the formation of microparticles by mixing a water soluble antigen with a solution of a water soluble polymer or hydrogel. U.S. Pat. No. 5,622,649 discloses W/O and W/O/W emulsions, but there is no disclosure of forming polymer particles. It is essential for the invention disclosed in U.S. Pat. No. 5,622,649 that no hydrophilic surfactant is present in the inner W phase. U.S. Pat. No. 5,622,649 does not disclose a water insoluble protein antigen in the inner W phase.

SUMMARY OF THE INVENTION

We have now developed a method which does allow one to use techniques which involve the formation of a W/O emulsion, in order to produce a polymer particle vaccine delivery system in which a water insoluble protein antigen is incorporated with the particles.

Accordingly, the present invention provides a method for producing polymer particles for use as a vaccine delivery system in which a water insoluble protein antigen is incorporated with particles comprising a polymer matrix, wherein the method comprises:

(a) mixing an aqueous phase (W) with an organic phase (O) that is immiscible with W to produce a W/O emulsion, in which the water insoluble protein is solubilised in the W phase using a solubilising agent, and the O phase comprises the matrix polymer in an organic solvent;

(b) forming droplets of said W/O emulsion by dispersing the emulsion in a fluid medium, and removing said solvent from the O phase of the W/O emulsion droplets to thereby form polymer particles incorporating the water insoluble protein antigen; and wherein in step (a) a stabilising agent is included in the W/O emulsion to promote the incorporation of the water insoluble protein with the polymer particles during step (b) by stabilising the W/O emulsion in the presence of said solubilising agent.

In addition, pursuant to the present invention we have for the first time provided a polymer particle vaccine delivery system in which a water insoluble protein antigen is incorporated with particles comprising a polymer matrix.

Furthermore, the present invention provides a vaccine composition comprising such a delivery system.

Another aspect of the present invention is the use of the delivery system in the manufacture of a vaccine composition, for the treatment of Helicobacter infection in a mammalian host, eg a human.

The present invention also relates to the use of the delivery system in the manufacture of a vaccine composition, for preventing or reducing the risk of Helicobacter infection in a mammalian host.

Figure 5:
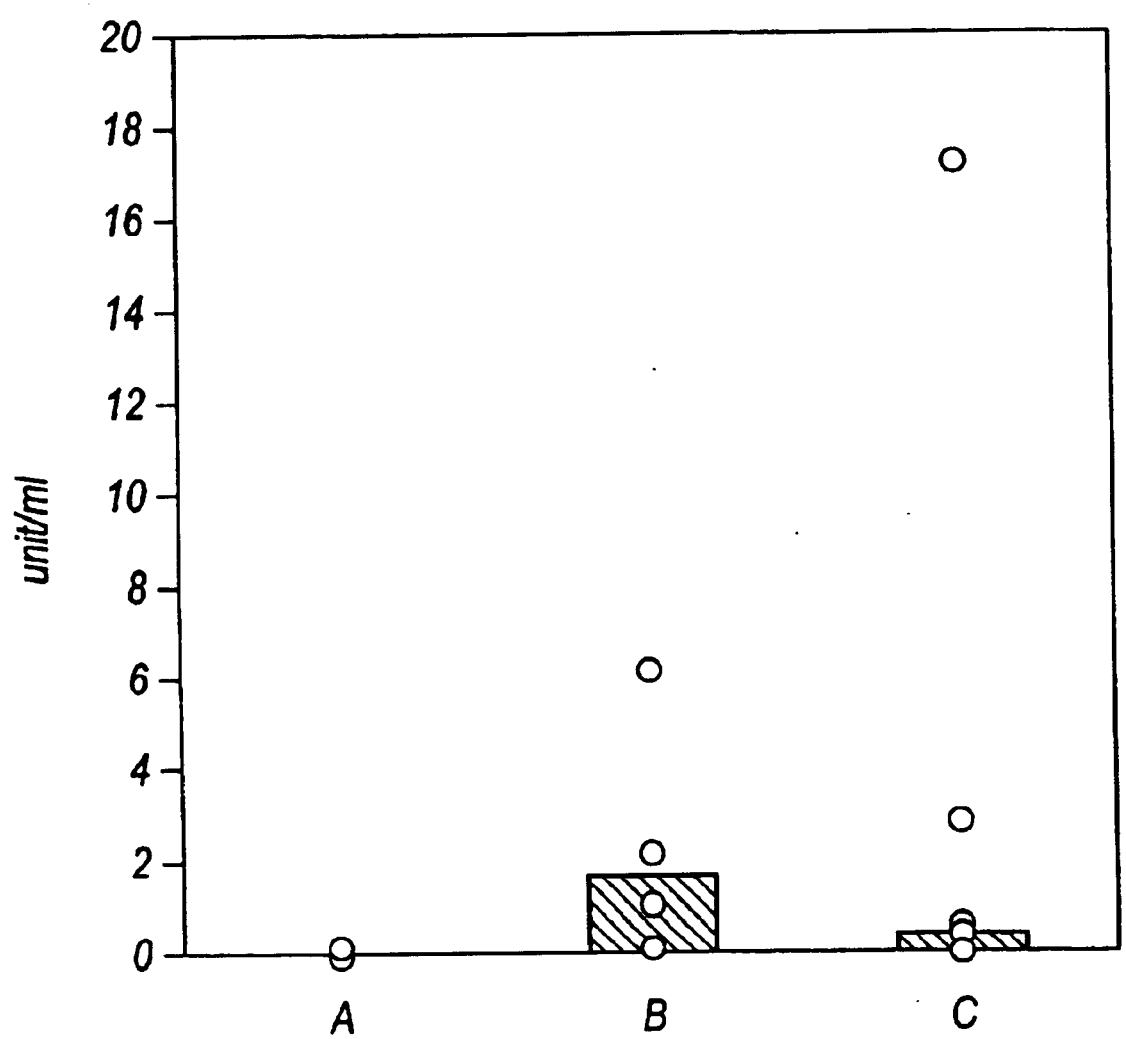
FIG. 5 shows the serum IgG2a results after intraduodenal immunisation with (i) HpaA co-administered with Cholera toxin (CT); or (ii) HpaA incorporated with PLG particles according to the invention. The bars represent the median of a group of six animals.

Legend to FIG. 5 and abbreviations are as follows: units/ml=the mean of serum IgG2a levels of rats given three weekly i.p. immunisations with 100 μg HpaA and 25 μg Cholera toxin was arbitrarily set to 50 units/ml; HpaA+CT= 100 μg HpaA admixed with 25 μg Cholera toxin (n=4), HpaPLG=PLG formulation containing 100 μg HpaA (n=6).

Figure 6:
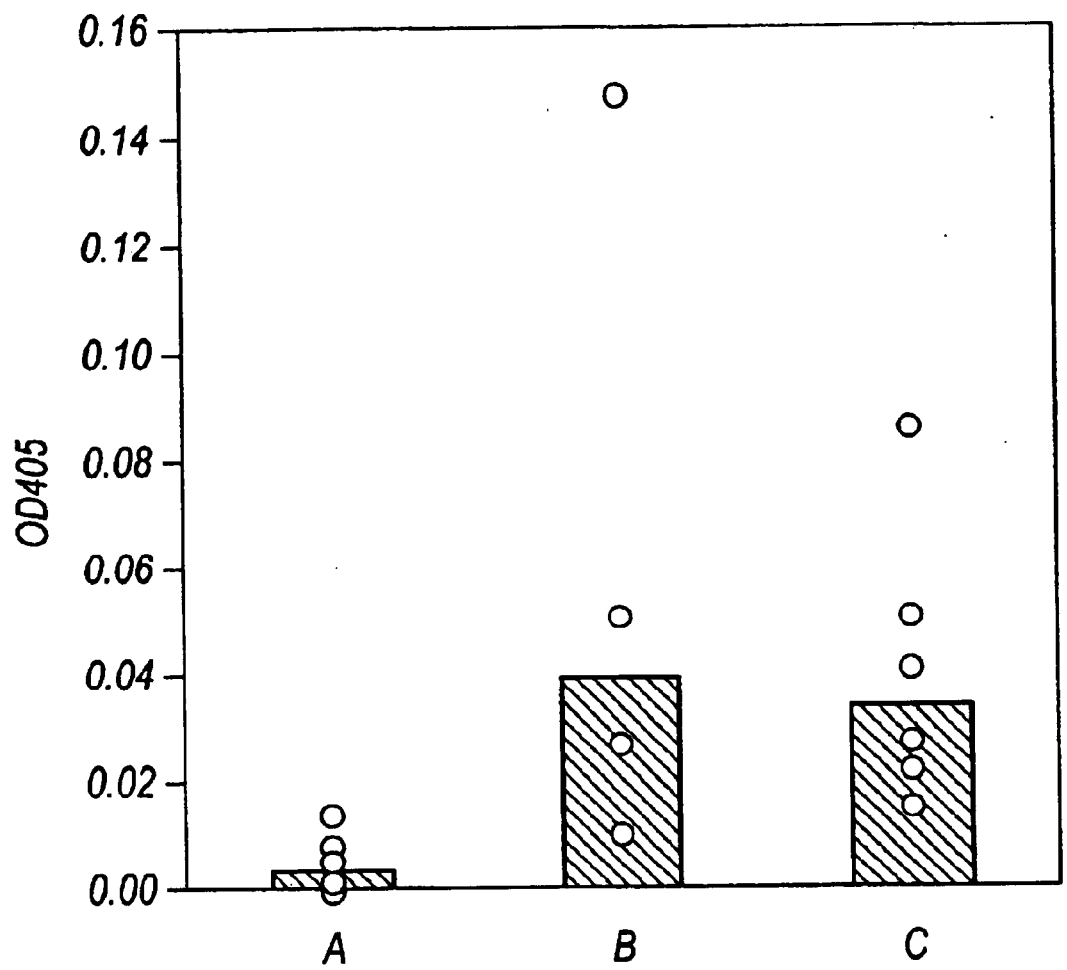

FIG. 6 shows the mucosal IgA results after intraduodenal immunisation with (i) HpaA co-administered with Cholera toxin (CT); or (ii) HpaA incorporated with PLG particles according to the invention. The bars represent the median of a group of six animals. "OD405" refers to the optical density read-out of anti-HpaA ELISA.

Legend to FIG. 6 and abbreviations are as follows: OD405=Optical density read-out of anti-HpaA ELISA; HpaA+CT=100 μg HpaA admixed with 25 μg Cholera toxin (n=4), HpaA/L121=PLG formulation containing 100 μg HpaA (n=6).

DETAILED DESCRIPTION OF INVENTION

As explained above, the present invention provides a polymer particle vaccine delivery system and a process for its production, in which a water insoluble protein is incorporated with particles comprising a polymer matrix. The polymer particles can be in the form of microparticles, such as microspheres.

The term "protein" in "water insoluble protein" is defined as a protein, polypeptide or peptide. The present invention contemplates the use of one or more proteins, so that the vaccine carrier system that is produced in some embodiments comprises more than one protein incorporated with the polymer matrix. In this case, at least one of the proteins is a water insoluble protein antigen; each of the other proteins can be water soluble or insoluble, and may or may not be antigenic (eg it may act as an adjuvant to promote the antigenicity of the water insoluble protein).

Water insoluble proteins are distinguished from water soluble proteins by their ability to associate with non-ionic detergents to form micelles, whereas water soluble proteins do not associate with such detergents to form micelles (A Practical Guide to Enzymology, C H Suelter, John Wiley & Sons Publishers, ISBN 0-471-86431-5, pp 71–72). Water insoluble protein/non-ionic detergent micelles can be easily detected, because the electrophoretic mobility of the protein when incorporated in the micelles is different from the protein's electrophoretic mobility in the absence of the non-ionic detergent. Since water soluble proteins do not associate with non-ionic detergents, there is no change in electrophoretic mobility for these proteins when in the presence or absence of a non-ionic detergent. The first step is to mix the protein to be tested with a non-ionic detergent, then with an ionic detergent. If micelles are formed (ie the protein is water insoluble), the ionic detergent subsequently added becomes incorporated in the micelles thus changing the electrophoretic mobility of the protein.

Another test for water insoluble proteins is as follows (A Practical Guide to Enzymology, C H Suelter, John Wiley & Sons Publishers, ISBN 0-471-86431-5, pp 71–72). The protein is dispersed in Triton®X-114 at 0° C. When the temperature of this detergent is raised above 20° C., its cloud point, separation into two phases occurs: an aqueous phase and a detergent phase. Water soluble proteins are recovered in the aqueous phase, whereas water insoluble proteins are found in the detergent phase.

In the method of the present invention, a W/O emulsion is formed in which the water insoluble protein is solubilised by the solubilising agent in the aqueous W phase, and the matrix polymer is dissolved in the O phase along with the organic solvent. Formation of the W/O emulsion can, for example, be effected by mixing the W phase containing the solubilised protein with the O phase containing the dissolved matrix polymer. The mixture is then emulsified, eg by ultra-sonication, stirring, extrusion, high shear mixing or high pressure homogenisation, while one or more suitable stabilising agents are included in the mixture. In this respect, (i) one or more stabilising agents can be included in the W phase, but not in the O phase, prior to mixing; or (ii) one or more stabilising agents can be included in each of the W and O phases prior to mixing; or (iii) one or more stabilising agents can be included in the O phase, but not in the W phase, prior to mixing. For forming the W/O emulsion, the W phase is mixed with the O phase in a ratio by volume of less than 1, more preferably 1:10,000 to 1:1, even more preferably, 1:100 to 1:1. The most preferred range is 1:4 to 1:1.5 for particularly good protein antigen incorporation.

In a second step, the stabilised W/O emulsion is dispersed in a fluid medium (ie, a liquid medium or gaseous medium such as air) to remove the organic solvent. This raises the concentration of the matrix polymer in the O phase so that the droplets "harden" and thereby form polymer particles incorporated with the water insoluble protein.

The second step can be carried out in various ways. In one embodiment, the method of the present invention can form part of a Double Emulsion (W/O/X) Solvent Evaporation Technique in which in the second step, the stabilised W/O emulsion is dispersed in a further liquid phase (X) which is immiscible with the O phase to produce a W/O/X double emulsion comprising stabilised W/O droplets from which the solvent is evaporated, thereby producing the polymer particles incorporating the water insoluble protein antigen. Dispersal of the stabilised W/O emulsion in the X phase can be carried out for example by ultra-sonication The X phase should be immiscible with the O phase or have only low (limited) miscibility with the O phase. Suitable examples for the X phase include aqueous phases, triglyceride (eg, sesame oil) and silicone oil.

In another embodiment, the method of the present invention is a Double Emulsion (W/O/X) Solvent Extraction Technique in which in the second step, a W/O/X double emulsion comprising W/O droplets is produced in a similar way to the Double Emulsion Solvent Evaporation Technique. In the Solvent Extraction embodiment, however, the X phase extracts the solvent from the O phase of the droplets, thereby producing the polymer particles incorporating the water insoluble protein antigen. As with the Solvent Evaporation Technique, suitable X phases for the Extraction Technique should have no or low (limited) miscibility with the O phase, and examples include an aqueous phase, triglyceride (eg, sesame oil) and silicone oil. In the Solvent Extraction Technique, the volume ratio of the X phase to the O phase is, however, considerably larger than with the Evaporation Technique.

If desired for these double emulsion techniques, one or more stabilising agents can be included in the X phase. The stabilising agents used for stabilising the first (W/O) emulsion can be used for this purpose. Optionally, removal of the solvent can be accelerated by stirring the double emulsion and/or warming (not to a protein antigen denaturing temperature) the double emulsion and/or reducing the pressure inside a vessel containing the double emulsion.

In yet another embodiment, the method of the present invention is a spray drying technique in which in the second step the stabilised W/O emulsion is dispersed in a gaseous medium (eg air) to form a spray of stabilised W/O emulsion droplets from which the solvent evaporates, thereby producing the polymer particles incorporating the water insoluble protein antigen. The W/O emulsion is usually dispersed by pumping it through a nozzle having a fine aperture. Spraying into a warmed chamber (ie not at protein denaturing temperature) can be effected in order to promote solvent evaporation.

Another embodiment involves the use of a fluid gas technique in the second step for forming the polymer particles. These techniques involve supercritical fluid technology. A supercritical fluid is a fluid simultaneously at or above its critical pressure and critical temperature. An example of a suitable fluid gas technique for the present embodiment is Gas Anti-Solvent Precipitation (GAS). In the conventional GAS technique, a substance of interest is dissolved in a solvent and a supercritical fluid (eg, carbon dioxide) is introduced into (mixed with) the solution, leading to the rapid expansion of the volume of the solution. As a result, the solvating power of the solvent decreases dramatically over a short period of time, thereby triggering the precipitation of particles (Cf. J W Tom and P G Debendetti, J. Aerosol. Sci, 22 (1991), 555–584; P G Debendetti et at, J Controlled Release, 24 (1993), 238–257; EP 437451 and EP 322687). When applied to the present invention, the stabilised W/O emulsion is used in place of the solution and a fluid gas is introduced with the solution to lead to a rapid expansion of the stabilised W/O emulsion, and thus formation of polymer particles incorporated the water insoluble protein antigen.

A modification of the GAS technique is the SEDS (Solution Enhanced Dispersion By Supercritical Fluid) technique (WO 95/01221 and WO 96/00610), and this can be used in the second step of the method of the invention for forming polymer particles. Here, one can use material in its supercritical or near supercritical state, or compressed gas as the "fluid gas". The supercritical fluid can be, for example, selected from carbon dioxide, nitrous oxide, sulphur hexafluoride, xenon, ethylene, chlorotrifluoromethane, ethane and trifluoromethane.

Other suitable techniques (modified anti-solvent (GAS) techniques) include: Precipitation with Compressed Anti-Solvents (PCA) procedure (Dixon et al., AIChE Journal, 1993, 39, 127–139; and Supercritical Anti-Solvent (SAS) procedure (Yeo et al., Biotech.Bioeng., 1993, 41, 341–346) or Aerosol Solvent Extraction System (ASES) (DE744329).

When fluid gas techniques have been used in the prior art, proteins have been included directly in an organic phase containing, eg ethanol (see EP-0542314; Tom et al., In Supercritical Fluid Engineering Science, ACS Symposium Series, 1993, 514, 238–257) or DMSO (see WO 96/29998), for co-precipitation with polymer. Disadvantages are the low solubility of proteins in organic solvents and supercritical fluids/modified supercritical flows (Stahl et at, "Dense Gas Results", Fluid Phase Equilibria, 1983, 10, 269); and protein denaturation (eg unfolding) by the organic solvent (Dill, K. A and Shortle, D. Ann. Rev. Biochem. 1991, 60, 795–825).

None of the prior art discloses the use of a W/O emulsion together with an anti-solvent fluid gas technique like GAS, SEDS, ASES, SAS and PCA, as in the preferred embodiment of the present invention. This avoids the disadvantages of the prior art techniques in which the protein is included directly in an organic phase, while providing an efficient method for producing polymer particles incorporated with a water insoluble protein, for use as a vaccine delivery system.

In the general method of the present invention, the water insoluble protein must be solubilised in the W phase, and for this a solubilising agent such as a hydrophilic surfactant or chaotropic agent can be used. More than one solubilising agent may optionally be used, ie one or more hydrophilic surfactant, one or more chaotropic agent, or one or more hydrophilic surfactant together with one or more chaotropic agent. The solubilising agent is hydrophilic, and by the term "hydrophilic surfactant" is meant a surfactant that solubilises a water insoluble protein antigen and is itself soluble in water (ie in the W phase); surfactants that are soluble in the O phase, but not in the W phase are not included in the term "hydrophilic surfactant". Preferably, the hydrophilic surfactant has a hydrophile-lipophile balance (HLB) of 10 or more; most preferably 13 or more. It will be readily apparent to the skilled person how to determine HLB values. In addition, reference is made to the following publications, which concern the determination of HLB values: Griffin, W. C., J. Soc. Cosmet. Chem. 1949, 1, 311; Griffin, W. C., J. Soc. Cosmet. Chem. 1954, 5, 249; Davies, J. T., Proc. 2nd Int. Cong. Surf. Acitivity; London, 1957, p. 417; Davies, J. T.; Rideal, E. K., Interfacial Phenomena; Academic: New York-San Fransisco-London, 1963. p 129; Davies, J. T., Progress in Surface Science; Danielli, J. F., Parkhurst, K. G. A., Riddford, A. C., Eds.; Academic: New York, 1964; Vol. 2, p 129.

Suitable temperatures at which the W/O emulsion is formed are from 0° C. to the boiling point on the O phase, but excluding temperatures that would denature the protein in the emulsion. Room temperature is often a suitable working temperature, although it should be mentioned that lower temperatures are preferable to slow down the dynamics of the emulsion.

Suitable hydrophilic surfactants include one or a mixture of surfactants selected from non-ionic, anionic, cationic and zwitterionic surfactants.

Suitable non-ionic surfactants can be selected from alkyl-glucopyranosides(eg, decyl-, dodecyl-, or octyl-glucopyranoside), alkyl-thioglucopyranosides (eg, octyl-thioglucopyranoside), alkyl-maltosides (eg, dodecyl- or lauryl maltoside), alkoyl-methyl glucamides (eg, heptanoyl-, octanoyl-, nonanoyl-, or decanoyl-N-methyl glucamide), polyoxyethylene alcohols (eg, $C_{11}E_8$, LuBrol PX or Brij series), polyoxyethylene alkyl phenols (eg, polyoxyethylene octyl phenols such as Nonidet P-40, Triton X-100), emulphogens, polyoxyethylene sorbitol esters (eg, Tween series), polyoxyethylene fatty acid esters, hydrophilic polyoxyethylene alkyl ethers and digitonin.

Suitable anionic surfactants can be selected from cholates (eg, sodium salts of glyco- or taurocholate), alkylsulphonates (eg, the sodium salt of pentyl-, octyl-, decyl-, dodecyl-, or myristylsulphonate), deoxycholates (eg, sodium deoxycholate), alkyl sulphates (eg, the sodium salt of octyl-, decyl-, dodecyl- or myristylsulphate), oligooxyethylene dodecyl ether sulphates and sodium dodecylsarcosinate.

Suitable cationic surfactants can be selected from alkylpyridinium salts (eg, a bromide or chloride of cetyl-, myristyl-, dodecyl- or decylpyridinium) and alkyltrimethylammonium salts (eg, cetyl-, myristyl-, dodecyl- or decyl-trimethylammonium bromide or chloride).

Suitable zwitterionic surfactants can be selected from CHAPS (3-[(3-cholamidopropyl dimethylammonio]-1-propanesulphonate), CHAPSO (3-[(3-Cholamidopropyl)-dimethylammonio]-2-hydroxy-1-propanesulphonate), BIGCHAP (N,N-bis[3-D-Gluconamidopropyl]-cholamide), deoxy BIGCHAP (N,N-bis[3-D-Gluconamidopropyl]-deoxycholamide), lyso phosphatidylcholine (eg, C16 lyso PC), N-tetradecyl-N,N-dimethyl-3-ammonia-1-propane sulphonate, alkylbetaines (eg, dodecylbetaine) and sulphobetaines.

Where a hydrophilic surfactant is used as a solubilising agent, a suitable range for the surfactant is to provide the surfactant in the W phase (in this case, we mean a solution including all of the components of the W phase except the protein(s) to be solubilised) at a concentration of 0.1 to 100 times, preferably 0.1 to 100 times, and more preferably 0.1 to 5 times the Critical Micelle Concentration (CMC) of the surfactant. Thus, the surfactant could for example be used at its CMC. Where a mixture of hydrophilic surfactants is used to solubilise, these ranges relate to the CMC of the mixture.

Suitable chaotropic agents include one or more of a perchlorate, thiocyanate, guanidine, chlorate, iodide, bromide, nitrate and urea.

While a hydrophilic solubilising agent is necessary to achieve solubilisation of the water insoluble protein in the aqueous (W) phase, the required hydrophilic character has the undesirable effect of destabilising any W/O emulsion droplets formed, by favouring a phase inversion to an O/W emulsion (ie, the aqueous phase being the outer continuous phase). According to the present invention, we include a stabilising agent in the W/O emulsion specifically to counter the undesirable effect of the solubilising agent (while retaining the agent's solubilising capacity) and exert a dominating effect which favours, and therefore stabilises, the W/O emulsion while forming the W/O droplets and forming the polymer particles. In this way, the stabilising agent brings about (promotes) the incorporation of the water insoluble protein with the polymer particles.

The common feature of all stabilising agents is that they adsorb to the W/O interface in the emulsion to prevent or reduce coalescence of the W droplets emulsified in the O phase. The stabilising agent may be soluble in the W phase and/or the O phase. More than one stabilising agent may optionally be included in the W/O emulsion.

Suitable stabilising agents that are soluble in the O phase, for example, increase the viscosity of the O phase of the W/O emulsion and/or are surface active agents having a predominantly hydrophobic character (hydrophobic surfactants). By the term "hydrophobic surfactant" is meant a stabilising surfactant that is overall predominantly hydrophobic and is soluble in the O phase, but not in the W phase.

Preferably, the stabilising agent is used in a proportion of from 0.01 to 99% by weight of the W/O emulsion, more preferably from 0.02 to 50 or 25% by weight of the W/O emulsion, and most preferably, from 0.05 to 5% by weight of the W/O emulsion. A particularly preferred embodiment is the use of 0.3% by weight of the W/O emulsion.

Preferably one or more stabilising agent is used, each agent being selected from polymers, polar lipids, and hydrophobic surfactants.

preferred stabilising polymer is selected from poly(vinyl pyrrolidone), poly(vinyl alcohol), polysaccharides, polyethyleneoxide and water soluble proteins (eg, gelatin; bovine serum albumin).

A preferred polar lipid is selected from cholesterol, phosphatidylcholine, phosphatidylethanolamine, phosphatidylglycerol, glycolipids and phosphatidic acid.

A stabilising agent can be used that is a non-ionic, hydrophobic surfactant selected from a sorbitan fatty acid ester (SPAN™ series), hydrophobic polyoxyethylene alkyl ether, sucrose ester, alkyl-glucopyranoside, polyglycerol polyricinoleate and block-copolymers of ethylene oxide with propyleneoxide and/or lactic acid.

A stabilising agent can be used that is an anionic, hydrophobic surfactant selected from an alkylsulphate salt, dialkylsulphosuccinate salt, alkylbenzene sulphonate salt and a fatty acid salt. Particularly preferable examples include sodium 1,4-bis (2-ethylhexyl) sulphosuccinate, calcium dioleate and aluminium or zinc stearate.

A stabilising agent can be used that is a cationic, hydrophobic surfactant selected from an alkyltrimethylammonium salt and a dialkyldimethylammonium salt (eg, distearyl dimethylammonium bromide).

In one preferred embodiment, a suitable stabilising composition is polyoxyethylene sorbitan fatty acid ester mixed with a sorbitan fatty acid ester. In another preferred embodiment, poly(vinyl pyrrolidone) and sodium 1,4-bis (2-ethylhexyl) sulphosuccinate are used together as stabilising agents.

In one embodiment of the present invention, the matrix polymer can be used as a stabilising agent by increasing the viscosity of the O phase. In this case, the matrix polymer can be added to the O phase up to the saturation point of the matrix polymer, with or without the use of another stabilising agent.

A suitable matrix polymer can be a homo- or co-polymer selected from polyesters, polyanhydrides, polyorthoesters, polycarbonates, polyamides, poly(amino acids), polyacetals, polycyanoacrylates, polyacrylates, biodegradable polyurethanes, non-erodable polyurethanes, polymers of ethylene-vinyl acetate, acyl substituted cellulose acetates, polysaccharides, polystyrenes, polyvinyl chloride, polyvinyl fluoride, poly(vinyl imidazole), chlorosulphonated polyolefins, polyethylene oxide, polyethers and polyoxalates. Optionally, mixtures of two or more of these polymers can be used in the O phase as matrix polymers.

In one embodiment, the polymer is an poly(esteramide).

Preferred matrix polymers are polyester homopolymers, such as polylactic acid, polyglycolic acid, polyhydroxybutyrate, poly(alpha hydroxyacids) and polycaprolactone.

Other preferred matrix polymers are polyester co-polymers, such as poly(lactide-co-glycolide), poly(lactic-co-glycolic acid), poly(hydroxybutyrate-hydroxyvalerate) and poly(lactide-co-caprolactone).

A particularly preferred matrix polymer is poly(D,L-lactide-co-glycolide).

In order to dissolve the matrix polymer in the O phase, one or more organic solvent may be used. Where we make reference to removing the organic solvent from the O phase in the method of the present invention, this should be construed as removing the organic solvent mixture, where more than one solvent is used. Suitable organic solvents depend on the particular matrix polymer used, and the skilled person can readily determine which solvent to use in order to dissolve the matrix polymer. Noteable examples of suitable solvents include methylene chloride, chloroform and ethyl acetate.

The method of the present invention can be used to produce polymer particles with an average diameter ranging from 0.01 to 1000 µm according to the volume size distribution. For subcutaneously implanted vaccine delivery systems, an average diameter from 0.1 to 100 µm according to the volume size distribution is preferred.

For mucosal delivery in vivo, an average diameter from 0.05 to 20 µm according to the volume size distribution is preferred, with a range of 0.1 to 10 µm according to the volume size distribution being the most suitable. Examples of suitable mammalian mucosa include the buccal, nasal, tonsillar, gastric, intestinal (small and/or large intestine), rectal and vaginal mucosa. Appropriate administration routes for these vaccines include oral, nasal, rectal and vaginal administration, with the oral, nasal and rectal routes being most preferred.

It will be readily apparent to the skilled person how to use the method of the present invention to produce particles of a desired size range. This skilled person could routinely, for example vary the relative volume ratios of the W and O phases and/or vary the thoroughness of emulsion homogenisation (eg, by varying the speed and/or duration of emulsion stirring).

When the delivery-system of the present invention is provided as part of a vaccine composition, it can optionally be so provided in combination with a suitable adjuvant. Suitable adjuvants are Cholera toxin (CT), *E. coli* heat labile toxin, cytokines and chemokines. The vaccine compositions can be used to treat and/or prevent a diseased state or infection (depending on the antigen(s) of the delivery system) in a mammalian patient by administering an immunologically effective amount of the composition to the patient. The term "immunologically effective amount" means an amount which elicits an immune response by the patient to the antigen(s) carried by the delivery system. An "immune response" is a response which eradicates, suppresses, prevents and/or reduces the risk of the infection or disease in the patient. Typically, an appropriate dose of the or each antigen per administration would be approximately 10 µg to 10 µg, preferably approximately 50 µg to 5mg, for oral administration. Suitable dosage forms include a frozen dispersion, freeze-dried particles or a liquid dispersion.

Examples of Preferred Embodiments of the Present Invention

The present invention can be used to provide a polymer particle delivery system that can be included in a vaccine composition for the treatment and/or prophylaxis of Helicobacter (in particular *Helicobacter pylory*) infection in a mammalian host. Thus such a vaccine can be administered to a patient, eg orally, in order to effect the treatment and/or prophylaxis. By "treatment", we mean the eradication or suppression of an existing Helicobacter infection in the host (in this respect, general reference is made to WO 96/40893). By "prophylaxis", we mean preventing or reducing the risk of the mammal becoming infected by Helicobacter after the vaccine has been administered.

The gram-negative bacterium *Helicobacter pylori* is an important human pathogen, involved in several gastroduodenal diseases. Colonisation of gastric epithelium by the bacterium leads to active inflammation and progressive chronic gastritis, with a greatly enhanced risk of progression to peptic ulcer disease.

In order to colonise the gastric mucosa, *H. pylori* uses a number of virulence factors. Such virulence factors comprise several adhesins, with which the bacterium associates with the mucus and/or binds to epithelial cells; ureases which helps to neutralise the acid environment; and proteolytic enzymes which makes the mucus more fluid.

Despite a strong apparent host immune response to *H. pylori*, with production of both local (mucosal) as well as systemic antibodies, the pathogen persists in the gastric mucosa, normally for the life of the host. The reason for this is probably that the spontaneously induced immune-response is inadequate or directed towards the wrong epitopes of the antigens.

In order to understand the pathogenesis and immunology of *H. pylori* infections, it is of great importance to define the antigenic structure of this bacterium. In particular, there is a need for characterisation of surface-exposed (like adhesins) and secreted proteins which, in many bacterial pathogens, have been shown to constitute the main virulence factors, and which can be useful for the diagnosis of *H. Pylori* and in the manufacture of vaccine compositions. Monoclonal antibodies (MAbs) against membrane preparations of *H. pylori* have been disclosed by Bölin et al. (1995) J. Clin. Microbiol. 33, 381–384. One of these MAbs, designated HP30-1:1:6, reacted with a 30 kDa protein which was shown to be exposed on the surface of intact bacteria and to have properties like that of an adhesin.

When the method of the present invention is used during the production of a vaccine for the treatment and/or prophylaxis of Helicobacter infection, the water insoluble protein antigen is a Helicobacter protein or antigenic fragment thereof Preferably, the protein antigen is a *Helicobacter pylori* protein or antigenic fragment thereof (eg, a membrane-associated or membrane-bound antigen). A Helicobacter protein that is a protein expressed on the outer surface of Helicobacter provides a particularly good antigen for incorporation with the polymer matrix of the vaccine delivery system.

Whenever stressed or threatened, the *H. pylori* cell transforms from a bacillary to a coccoid form. In the coccoid form, the *H. pylori* cell is much less sensitive to antibiotics and other anti-bacterial agents. Circumstantial evidence indicate the *H. pylori* might be transmitted between individuals in this form, possibly via water or direct contact. An efficient vaccine composition should therefore elicit an immune response towards both the coccoid and the bacillary form of *H. pylori*. Preferred water insoluble Helicobacter proteins for the vaccine delivery system are therefore such proteins that are exposed on the surface of both the dividing (bacillary) and resting (coccoid) forms of Helicobacter.

Since systemic immunity probably only plays a limited role in protection against mucosal Helicobacter infection, it is also important that the vaccine composition will enhance protective immune mechanisms locally in the stomach.

Reference is made to WO 96/38475 which discloses an antigen that is a putative adhesin and is exposed on the surface of both the dividing (bacillary) and resting (coccoid) forms of *Helicobacter pylori*. The disclosure of WO 96/38475 is hereby incorporated by reference, and in particular the expression methods disclosed therein are expressly incorporated by reference and the skilled person is directed to these specific disclosures for further guidance. We refer to this antigen as a HpaA protein. Cloning of a hpaA sequence, which reportedly coded for a 20 kDa receptor-binding subunit of the N-acetylneuraminyllactose-binding fibrillar hemagglutinin (NLBH) of *H. pylori*, has been disclosed by Evans et al. (1993) J. Bacteriol. 175, 674–683. Reference is also made to P W Toole et al, Bacteriology Vol. 177, No. 21, Nov. 1995; and Jones, A. C., Logan, R. P., Foynes, S., Cockayne, A., Wren, B. W. and Penn, C. W., J. Bacteriol. 179 (17), 5643–5647 (1997) which concern HpaA proteins.

The HpaA protein is expressed by all *H. pylori* strains tested, and antibodies created towards this protein do not cross-react with common endogenous human bacteria of other species or with selected human tissues including the gastric mucosa. Thus being a well conserved putative adhesin with immunogenic properties, the HpaA protein is useful both for the detection of *H. pylori* infections as well as for the manufacture of vaccine compositions. Table 1 shows a comparison of HpaA amino acid sequences derived from 4 different strains of *H. Pylori*. It can be seen from the table that the sequence is highly conserved amongst different strains.

by the enzyme prolipoprotein glyceryltransferase to give a product II, followed by the addition of two lipid chains to give product III. The latter step is catalysed by at least one transacylase. The signal sequence of the lipidated product III is then cleaved off by prolipoprotein signal peptidase to give a product IV (it is believed that the signal sequence corresponds to positions 1 to 27 in SEQ ID NO's. 2 and 4). A third lipid chain is then added to this protein by phospholipid diglyceride lipoproteintransacylase to give a "fully lipidated" protein product (V). In the method of the present invention, a lipidated form of HpaA can be used as the water

TABLE 1

| | |
|---|---|
| Evans (8826) | MKTNGHFKDFAWKKCLLGTSVVALLVGCSPHIIETNEVALKLNYHPASEKVQALDEKILL (SEQ ID NO:5) |
| GTC (J99) | MKTNGHFKDFAWKKCFLGASVVALLVGCSPHIIETNEVALKLNYHPASEKVQALDEKILL (SEQ ID NO:6) |
| Trust (17874) | MKTNGHFKDFANKKCLLGASVGALLVGCSPHIIETNEVALKLNYHPASEKVQALDEKILL (SEQ ID NO:7) |
| Penn (11637) | MRANNHFKDFAWKKCLLGASVVALLVGCSPHIIETNEVALKLNYHPASEKVQALDEKILL (SEQ ID NO:8) |
| TIGA (26695) | MKANMHFKDFAWKKCLLGASVVALLVGCSPHIIETNEVALKLNYHPASEKVQALDEKILL (SEQ ID NO:9) |
| | *..*.********.. ********************************** |
| Evans (8826) | LKPAFQYSDNIAKEYENKFKNQTTLKVEEILQNQGYKVINVDSSDXDDFSFAQKKEGYLA (SEQ ID NO:10) |
| GTC (J99) | LRPAFQYSDNIAKEYENKFKNQTTLKVEEILQNQGYKVINVDSSDKDDFSFAQKKEGYLA (SEQ ID NO:11) |
| Trust (17874) | LRPAFQYSDNIAKEYENKFKNQTVLKVEQILQNQGYKVINVDSSDKDDFSFAQKKEGYLA (SEQ ID NO:12) |
| Penn (11637) | LRPAFQYSDNIAKEYENKFKNQTALKVEQILQNQGYKVISVDSSDKDDFSFAQKKEGYLA (SEQ ID NO:13) |
| TIGR (26695) | LRPAFQYSDNIAKEYESKFKNQTALKVEQILQNQGYKVISVDSSDKDDLSFSQKKEGYLA (SEQ ID NO:14) |
| Evans (8826) | VAMIGEIVLRPDPKRTIQKKSEPGLLFSTGLDKMEGVLIPAGFVKVTILEPMSGESLDSF (SEQ ID NO:15) |
| GTC (J99) | VAMNGEIVLRPDPKRTIQKKSEPGLLFSTGLDKMEGVLIPAGFVKVTILEPMSGESLDSF (SEQ ID NO:16) |
| Trust (17874) | VAMNGEIVLRPDPKRTIQKKSEPGLLFSTGLDKMEGVLIPAGFVKVTILEPMSGESLDSF (SEQ ID NO:16) |
| Penn (11637) | VAMNGEIVLRPDPKRTIQKKSEPGLLFSTGLDKMEGVLIPAGFIKVTILEPMSGESLDSF (SEQ ID NO:17) |
| TIGR (26695) | VAMNGEIVLRPDPKRTIQKKSEPGLLFSTGLDKMEGVLIPAGFVKVTILEPMSGESLDSF (SEQ ID NO:16) |
| | * *******************************.************** |
| Evans (8826) | TMDLSELDIQEKFLKTTHSSHSGGLVSTMVKGTDNSNDAIKSALNKIFASIMQENDKKLT (SEQ ID NO:18) |
| GTC (J99) | TMDLSELDIQEKFLKTTHSSHSGGLVSTMVKGTDNSNDAIKSALNKIFASIMQEMDKKLT (SEQ ID NO:18) |
| Trust (17874) | TMDLSELDIQEKFLKTTHSSHSGGLVSTMVKGTDNSNDAIKSALNKIFGSIMQEIDKKLT (SEQ ID NO:19) |
| Penn (11637) | TMDLSELDIQEKFLKTTHSSHSGGLVSTMVKGTDNSNDAIKSALNKIFANIMQEIDKKLT (SEQ ID NO:20) |
| TIGR (26695) | TMDLSELDIQEKFLKTTHSSHSGGLVSTMVKGTDNSNDAIKSALNKIFANIMQEIDKKLT (SEQ ID NO:20) |
| | *************************************...*** |
| Evans (8826) | QRNLESYQKDAKELKNKRNR (SEQ ID NO:21) |
| GTC (J99) | QRNLESYQKDAKELKNKRNR (SEQ ID NO:21) |
| Trust (17874) | QKNLESYQKDAKELKGKRNR (SEQ ID NO:22) |
| Penn (11637) | QKNLESYQKDAKELKGKRNR (SEQ ID NO:22) |
| TIGR (26695) | QKNLESYQKDAKELKGKRNR (SEQ ID NO:22) |

The accompanying sequence listing shows a nucleic acid sequence (SEQ ID NO. 1) comprising the hpaA gene and the amino acid sequence (SEQ ID NO. 2) of a HpaA protein that is predicted to be 29 kDa, which includes a signal sequence and is encoded by the hpaA gene. Note that in SEQ ID NO's. 1 and 2, amino acid 222 is serine; this position can alternatively be arginine (see SEQ ID NO's. 3 and 4).

Referring to the formulae below, the predicted 29 kDa protein is shown as formula I. We believe that this is further processed in Helicobacter as follows. Protein I is processed insoluble protein. Most preferably, a fully lipidated form of HpaA is used (ie, one with at least 3 lipid chains, eg three C16 chains as in protein V). The protein part (referred to here as the "protein core") of product V, therefore, corresponds to the full length protein (1) minus the signal sequence. It is contemplated that the protein core (or even antigenic fragments thereof) can be synthesised in vitro and lipidated (not necessarily in the same pattern as product V), and this lipidated HpaA protein can be used as a water insoluble protein antigen in the present invention.

Met—Leu-Ala-Gly-Cys—Protein (SEQ ID NO:23)  I

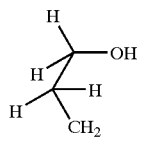

Met—Leu-Ala-Gly-Cys—Protein (SEQ ID NO:24)  II

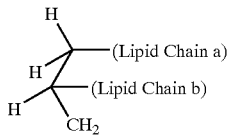

Met—Leu-Ala-Gly-Cys—Protein (SEQ ID NO:25)  III

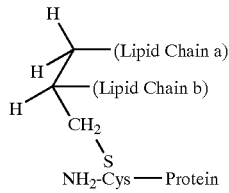

NH₂-Cys—Protein  IV

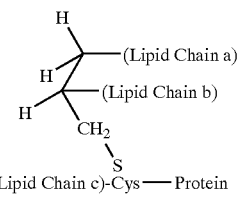

(Lipid Chain c)-Cys—Protein  V

Where "(Lipid Chain a)" denotes:-

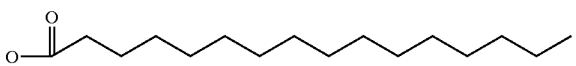

"(Lipid Chain b)" denotes:-

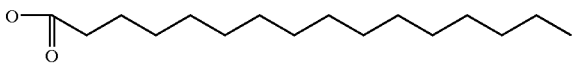

"(Lipid Chain c)" denotes:-

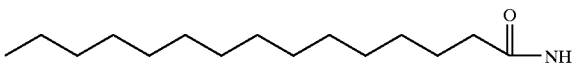

Preferably, where a lipidated HpaA protein antigen is used as a water insoluble protein in the present invention, the protein part of the antigen has an amino acid sequence that is identical or substantially similar to positions 28 to 260 of the amino acid sequence set out in SEQ ID NO.2 or 4, but of course retaining antigenic activity suitable for use in a vaccine for prophylaxis and/or treatment of Helicobacter infection in a mammalian host (including the ability of the antigen to elicit a mucosal as well as a systemic immune response against Helicobacter in a mammalian host). By "substantially similar" we mean one or more of the following: the protein part includes an amino acid sequence at least 60%, 70%, 80%, 90%, 95%, 98% or 99% homologous to positions 28 to 260 of the amino acid sequence set out in SEQ ID NO.2 or 4; the protein part includes at least 5, 10, 20, 50, 100, 150 or 200 contiguous amino acid residues of positions 28 to 260 of the amino acid sequence set out in SEQ ID NO. 2 or 4, but retaining antigenic activity (ie at least one immunogenic epitope, with or without fusion to an inert or immunologically active carrier polypeptide) suitable for use in a vaccine for prophylaxis and/or treatment of Helicobacter infection in a is mammalian host; the protein part of the antigen includes an amino acid sequence differing in amino acid sequence by 1, 2, 3, 5, or 10 residues from positions 28 to 260 of the amino acid sequence set out in SEQ ID NO. 2 or 4, but retaining antigenic activity suitable for use in a vaccine for prophylaxis and/or treatment of Helicobacter infection in a mammalian host.

Specific mention is made to the section in WO 96/38475 describing how to identify and analyse epitopes of the HpaA protein.

The protein antigen used in the invention may be prepared from Helicobacter cells and/or produced by recombinant techniques.

Although in the formulae above, a fully lipidated HpaA protein is shown where each of the three lipid chains has 16 carbons, each lipid chain can be a C12 to C20 lipid chain. C16 and C18 lipid chains are preferred, and most preferably, the HpaA antigen has at least one C16 chain and at least one C18 chain. It is known that lipid modification can determine immunological properties of bacterial lipoproteins (see Weis, J J et al (1994) Infection and Immunity, vol. 62, 4632–4636). Where the protein has three C16 lipid chains (protein V above), the protein has a predicted weight of 27 kDa. The weight of HpaA protein may, however, vary depending on the lipidation pattern of the protein.

Preparation of Polymer Particles Incorporated with HpaA

The following examples illustrate the incorporation of HpaA with either PLGA particles or PHB (poly(3-hydroxybutyrate)) particles.

Analysis of Emulsions

The visual appearance of the double emulsions was studied with light microscopy (Leica microscope, DMRBE, Leica Mikroskopie und Systeme GmbH, Germany).

Analysis of Particles

The particle size, form and morphology were studied with scanning electron microscopy. Degree of agglomeration and particle size distribution were analysed with an Aerosizer (Aerosizer®, Amherst Process Instruments, Hadley, Mass., USA). This measurement technique is based on the determination of the aerodynamic time-of-flight for the particles. The density of the particles assumed to be equal to the polymers density, 1.25 g/cm³ for PHB.

Particle sizes were also determined by means of laser diffraction, using a Coulter LS130 (Coulter Corp, Hialeah, Fla., USA).

Determination of HpaA Loading

PHB Particles a) Total Protein Content:

Particles (3–10 mg) were dissolved in 300 µl chloroform. SDS-laemmli (400 µl) was then added and the protein was extracted from the organic phase to the water phase. The samples were shaken at 60° C. for 30 min. The water phase was heated to 95° C. for 15 min and the protein content analysed by polyacrylamide gel electrophoresis (SDS-PAGE). The SDS Laemmli reagent solution used in the protein analysis consisted of 1.25 ml TRIS HCl 2 M (pH 6.8) buffer solution, 5.05 g glycerol (99%), 0.8 g sodium dodecylsulphate (SDS), 1 ml 2-mercaptoethanol, 1 µl bromophenol blue and 10 ml water.

PLGA Particles a) Total Protein Content:

Particles (3–10 mg) were dissolved in 1 ml acetone. The protein precipitate was centrifuged for 15 minutes at 17

530×g, and about ⅔ of the supernatant was removed with a Hamilton syringe. Pure acetone was added in order to wash the sample twice. The remaining acetone was evaporated by vacuum centrifugation. SDS-Laemmli (200 μl) was added and the sample was heated to 95° C. for 15 minutes. The analysis of the protein content was performed by SDS-PAGE.

b) Analysis of the Amount of the Surface Associated Protein:

Analysis of the amount of protein associated to the surface was performed according to Rafati et al. (*Journal of Controlled Release* 1997 43, 89–102). To 5–6 mg of particles was added 2 ml 2% (w/v) SDS in water. The samples were shaken for 4 hours. The samples were then centrifuged at 2700×g for 3 minutes and the water phase removed to a new tube. The water was evaporated by vacuum centrifugation and 1 ml Laemmli (without SDS) was added. The water phase was heated to 95° C. for 15 min and the protein amount analysed by SDS-PAGE.

A: Double Emulsion Techniques

In the following examples, the 27 kDa lipidated form of HpaA (ie protein V above) was used. The HpaA polypeptide antigen was obtained in-house.

EXAMPLE 1

PLGA particles incorporated with the HpaA protein were produced to an average diameter of approximately 10 μm according to the volume size distribution, which is well suited to gastric mucosal delivery.

Materials & Methods

Materials: PL(D,L)GA (poly D,L-lactide-co-glycolide, 50:50, Mw 14400, RESOMER™ 502, Boehringer Ingelheim), DCM (dichloromethane), PVA (poly(vinyl alcohol), Mw 13-23 000, Aldrich), PVP (poly(vinyl pyrrolidone), Mw 10 000, Aldrich), acetone, NOG (n-Octyl-glucopyranoside, SIGMA), TRIS buffer salts and Laemmli sample buffer were used as purchased. The water was of ELGA quality (18.2 MΩ).

Methods: 950 μl of a 2% (w/w) NOG solution (100 mM, pH8 TRIS buffer), with the antigen, was mixed with 1050 μl 2% (w/w) PVP (aq). The solution was dispersed in 3900 μl 3% (w/w) PLGA (DCM) by homogenization at 20000 rpm for 3 min. The formed $W_1$/O emulsion was further dispersed in 140 g 10% (w/w) PVA (aq) by homogenization at 5 000 rpm for 5 min. The formation of double emulsion droplets was confirmed by light microscopy. The ($W_1$/O)/$W_2$ double emulsion was stirred overnight to allow the DCM to evaporate. The particles were collected by centrifugation and washed with water to remove the PVA.

The volume average diameter of the particles was determined to 9.4 μm by laser diffraction measurements. The degree of protein antigen incorporation with the PLGA particles was determined by SDS-PAGE to be 49% of the protein that was initially added.

After protein content analysis, the antigen concentration in the suspension was adjusted to 0.33 g/l.

Figure 1:
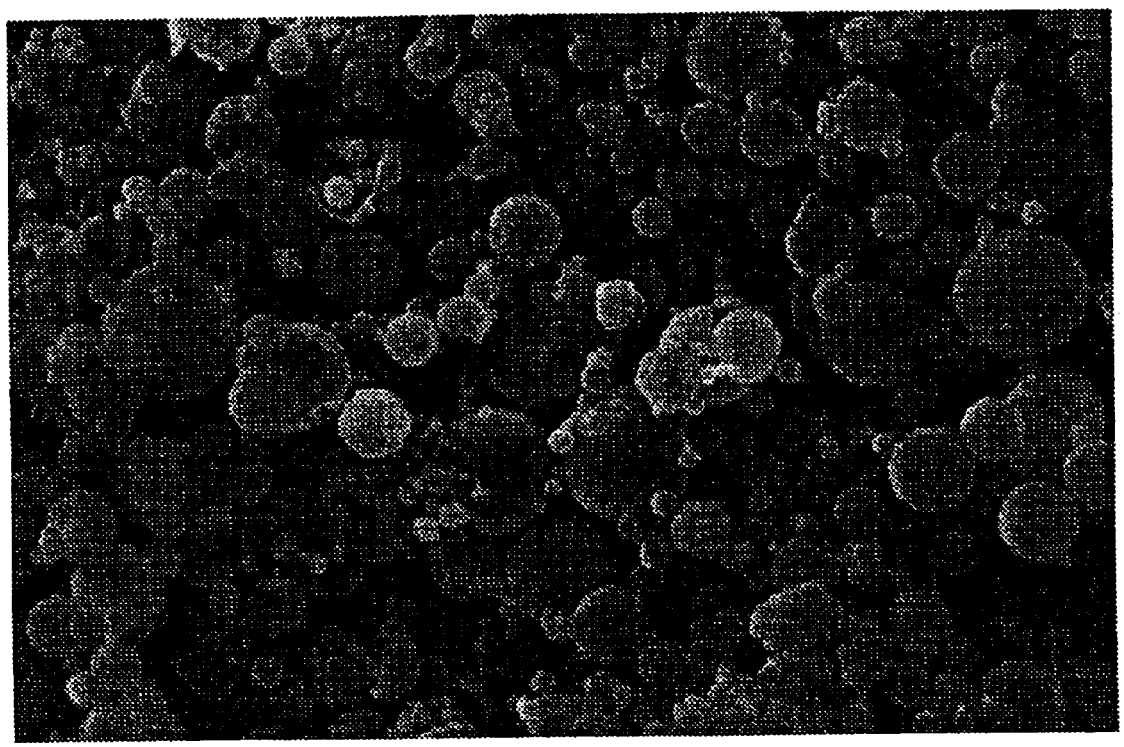
FIG. 1 is an SEM image of PLGA particles incorporated with HpaA according to the invention. The particles have an average diameter of 10 μm.
Figure 2:
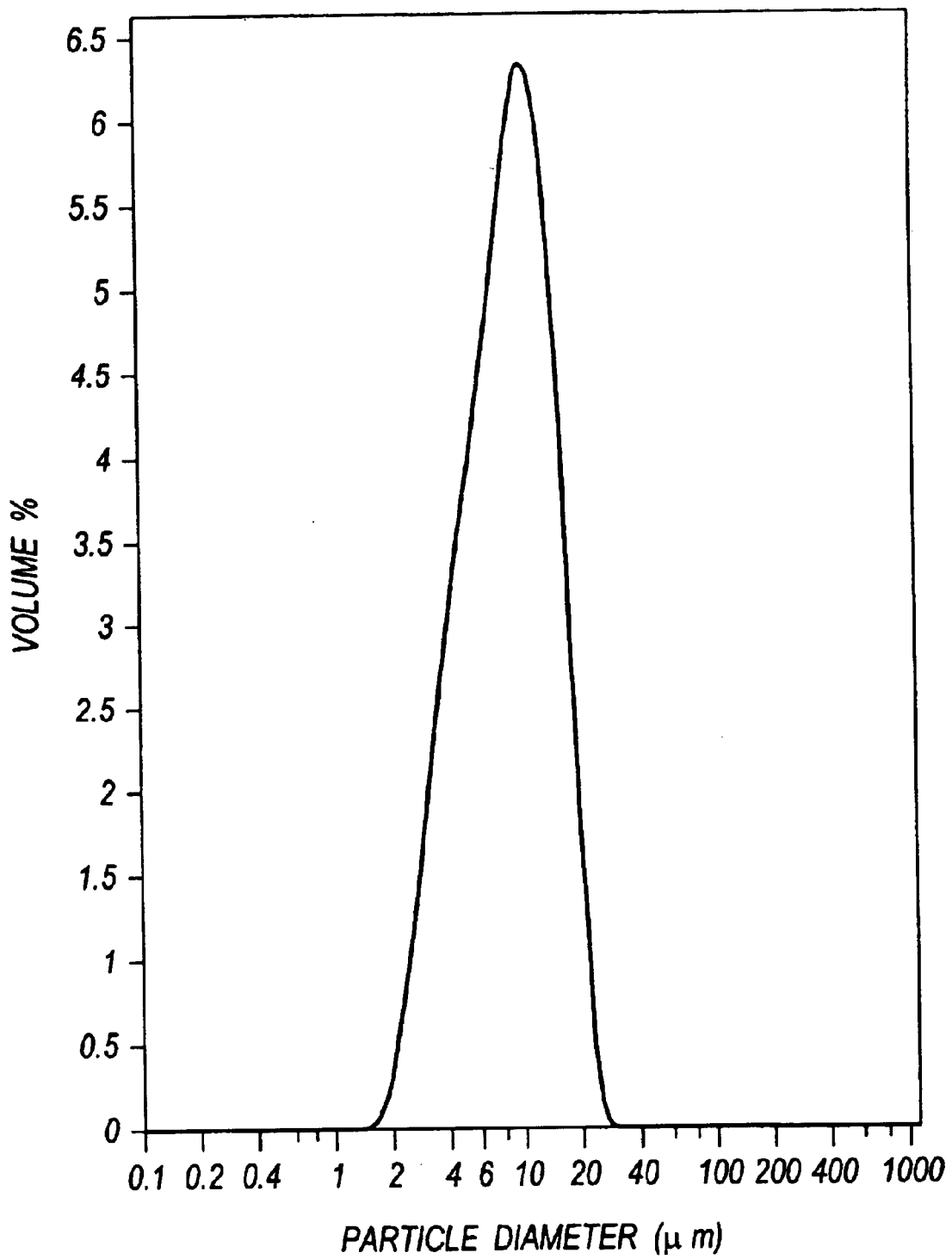
FIG. 2 is a particle size graph for PLGA particles produced according to the invention. The particles are incorporated with HpaA and have an average diameter of 10 μm.

Results: FIG. 1 shows an SEM image for particles of Example 1. FIG. 2 shows the particle size distribution of particles of Example 1.

EXAMPLE 2

PLGA particles incorporated with the HpaA protein were produced to an average diameter of approximately 300 nm according to the volume size distribution, which is well suited to gastric mucosal delivery.

Materials & Methods

Materials: PL(D,L)GA (poly D,L-lactide-co-glycolide, 50:50, Mw 14400, RESOMER™ 502, Boehringer Ingelheim), DCM (dichloromethane), PVA (poly(vinyl alcohol), Mw 13-23000, Aldrich), PVP (poly(vinyl pyrrolidone), Mw 10 000, Aldrich), AOT (sodium 1,4-bis (2-ethylhexyl) sulphosuccinate, SIGMA), acetone, NOG (n-Octyl-glucopyranoside, SIGMA), TRIS buffer salts and Laemmli sample buffer were used as purchased. The water was of ELGA quality (18.2 MΩ).

Methods: 950 μl of a 2% (w/w) NOG solution (10 mM, pH8 TRIS buffer), with the antigen, was mixed with 1050 μl 2% (w/w) PVP (aq). The solution was dispersed in 3900 μl of a DCM solution, containing 3% (w/w) PLGA and 0.4% (w/w) AOT, by homogenization at 20 000 rpm for 3 min. The formed $W_1$/O emulsion was further dispersed in 140 g 10% (w/w) PVA (aq) by homogenization at 5 000 rpm for 5 min. The formation of double emulsion droplets was confirmed by light microscopy. The ($W_1$/O)/$W_2$ double emulsion was stirred overnight to allow the DCM to evaporate. The particles were collected by centrifugation, washed with water to remove the PVA and freeze dried.

The volume average size diameter of the particles was determined to 0.35 μm/1.7 μm (bimodal distribution) by laser diffraction measurements. The HpaA content (% of dry particles) was calculated to 0.3% (w/w).

Figure 3:
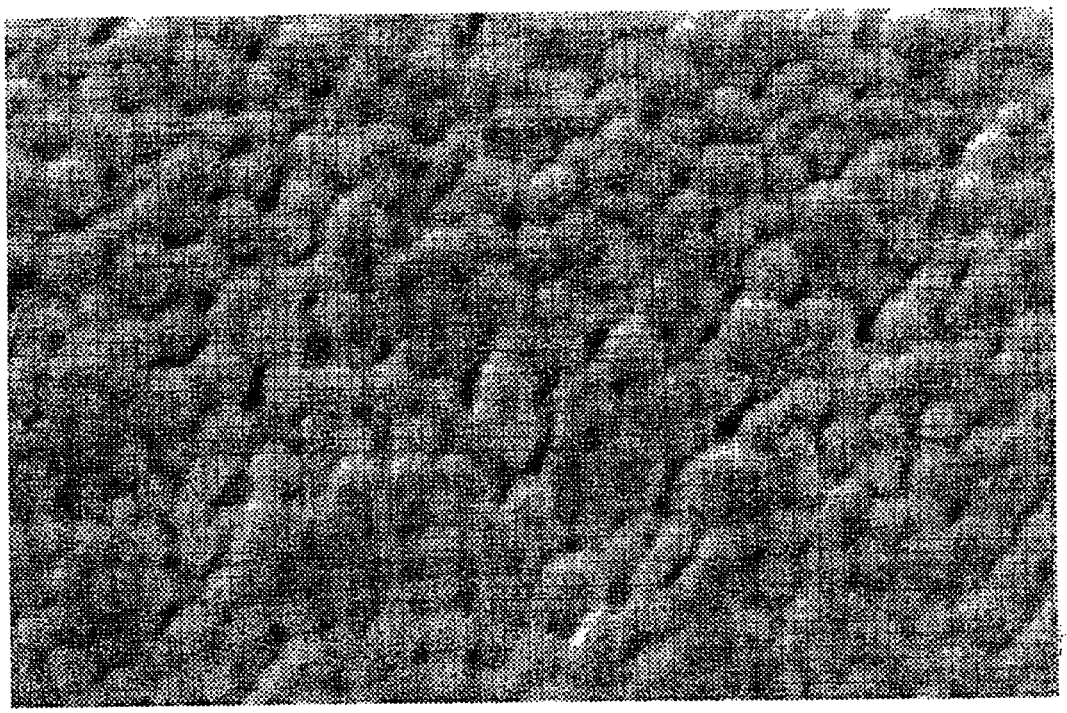
FIG. 3 is an SEM image of PLGA particles incorporated with HpaA according to the invention. The particles have an average diameter of 300 nm.
Figure 4:
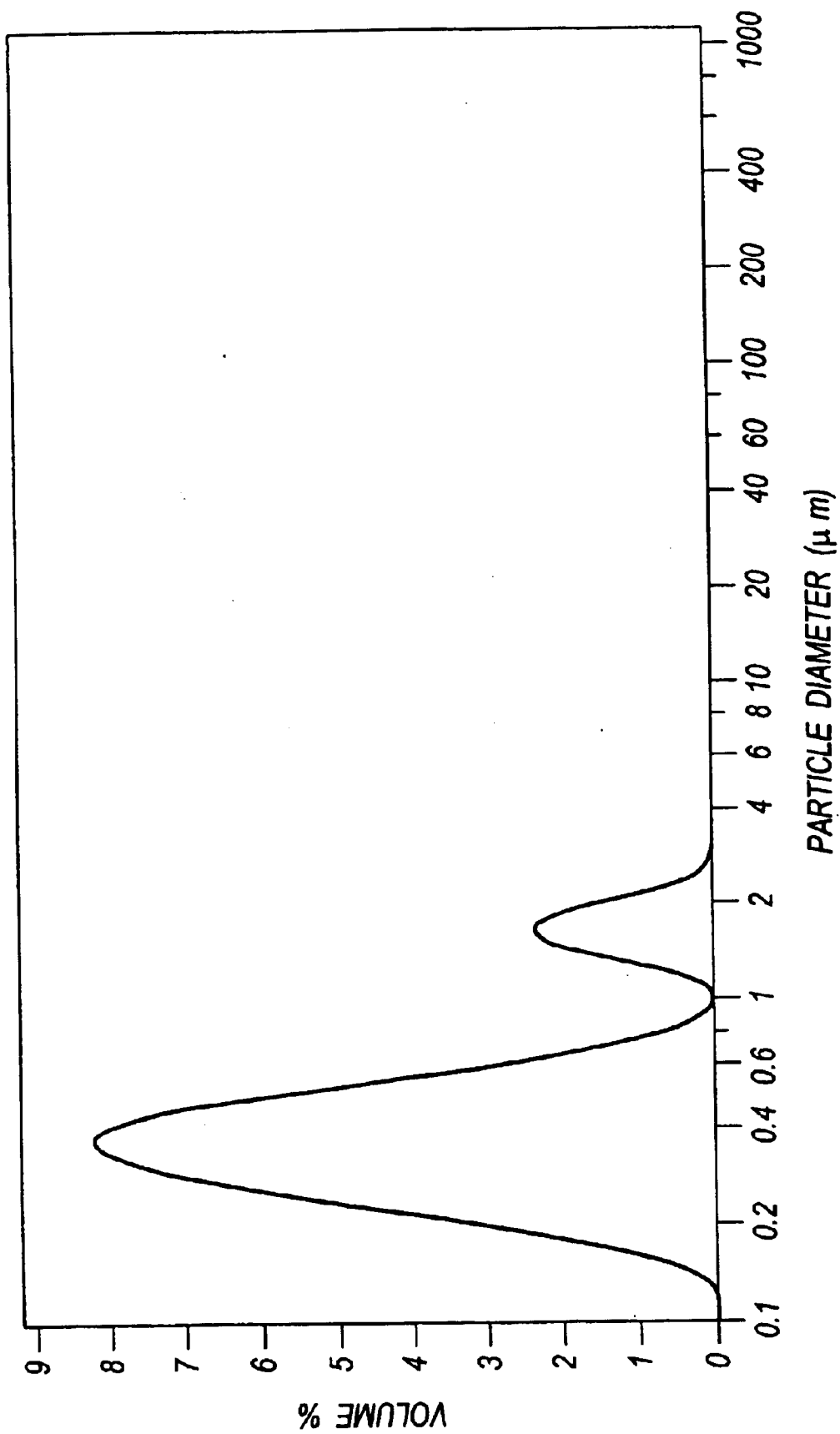
FIG. 4 is a particle size graph for PLGA particles produced according to the invention. The particles are incorporated with HpaA and have an average diameter of 300 nm.

Results: FIG. 3 shows an SEM image for particles of Example 2. FIG. 4 shows the particle size distribution of particles of Example 2.

EXAMPLE 3

PLGA particles incorporated with the HpaA protein were produced to an average diameter of approximately 300 nm according to the volume size distribution, which is well suited to gastric mucosal delivery.

Materials & Methods

Materials: PL(D,L)GA (poly D,L-lactide-co-glycolide, 50:50, Mw 14400, RESOMER™ 502, Boehringer Ingelheim), DCM (dichloromethane), PVA (poly(vinyl alcohol), Mw 13-23 000, Aldrich), PVP (poly(vinyl pyrrolidone), Mw 10 000, Aldrich) and AOT (sodium 1,4-bis (2-ethylhexyl) sulphosuccinate, SIGMA) were used as purchased. The water was of ELGA quality (18.2 MΩ).

Methods: 500 μl of a 2% (w/w) NOG solution (10 mM, pH8 TRIS buffer), with the antigen, was mixed with 500 μl 2% (w/w) PVP (aq). The solution was dispersed in 1950 μl of a DCM solution, containing 3% (w/w) PLGA and 0.4% (w/w) AOT, by homogenization at 20 000 rpm for 3 min. The formed $W_1$/O emulsion was further dispersed in 70 g 10% (w/w) PVA (aq) or 70 g 2% (w/w) PVA by homogenization at 5 000 rpm for 5 min. The formation of double emulsion droplets was confirmed by light microscopy. The ($W_1$/O)/$W_2$ double emulsion was stirred overnight to allow the DCM to evaporate. The particles were washed with water by cross flow filtration.

The volume average size of the particles was determined to 0.35 μm/1.7 μm (bimodal distribution, 10% (w/w) PVA) and 0.29 μm (2% (w/w) PVA) by laser diffraction measurements.

EXAMPLE 4

PLGA particles incorporated with the HpaA protein were produced to an average diameter of 6 μm according to the volume size distribution, which is well suited to gastric mucosal delivery.

Materials & Methods

Materials: PL(D,L)GA (poly D,L-lactide-co-glycolide, 50:50, Mw 14400, RESOMER™ 502, Boehringer Ingelheim), DCM (dichloromethane), PVA (poly(vinyl alcohol), Mw 13-23 000, Aldrich), PVP (poly(vinyl pyrrolidone), Mw 10 000, Aldrich). The water was of ELGA quality (18.2 MΩ).

Methods: 500 µl of a 2% (w/w) NOG solution (10 mM, pH8 TRIS buffer), with the antigen, was mixed with 100 µl 10% (w/w) PVP (aq). The solution was dispersed in 1950 µl 3% (w/w) PLGA (DCM) by homogenization at 20 000 rpm for 3 min. The formed $W_1/O$ emulsion was further dispersed in 70g 10% (w/w) PVA (aq) by homogenization at 5 000 rpm for 5 min. The formation of double emulsion droplets was confirmed by light microscopy. The $(W_1/O)/W_2$ double emulsion was stirred overnight to allow the DCM to evaporate.

The volume average size of the particles was determined to 6 µm by laser diffraction measurements.

EXAMPLE 5

PLGA particles incorporated with the HpaA protein were produced to an average diameter of approximately 6 µm according to the volume size distribution, which is well suited to gastric mucosal delivery.

Materials & Methods

Materials: PL(D,L)GA (poly D,L-lactide-co-glycolide, 50:50, Mw 14400, RESOMER™ 502, Boehringer Ingelheim), DCM (dichloromethane), PVA (poly(vinyl alcohol), Mw 13-23 000, Aldrich), PVP poly(vinyl pyrrolidone), Mw 10 000, Aldrich) and AOT (sodium 1,4-bis (2-ethylhexyl) sulphosuccinate, SIGMA) were used as purchased. The water was of ELGA quality (18.2 MΩ).

Methods: 500 µl of a 2% (w/w) NOG solution (10 mM, pH8 TRIS buffer), with the antigen, was mixed with 100 µl 10% (w/w) PVP (aq). The solution was dispersed in 1900 µl of a DCM solution, containing 3% (w/w) PLGA and 0.26% (w/w) AOT, by homogenization at 20 000 rpm for 3 min. The formed $W_1/O$ emulsion was further dispersed in 70 g 10% (w/w) PVA (aq) by homogenization at 5 000 rpm for 5 min The formation of double emulsion droplets was confirmed by light microscopy. The $(W_1/O)/W_2$ double emulsion was stirred overnight to allow the DCM to evaporate.

The volume average size of the particles was determined to 5.8 µm by laser diffraction measurements.

EXAMPLE 6

PLGA particles incorporated with the HpaA protein were produced to an average diameter of 4 µm according to the volume size distribution, which is well suited to gastric mucosal delivery.

Materials & Methods

Materials: PL(D,L)GA (poly D,L-lactide-co-glycolide, 50:50, Mw 14400, RESOMER™ 502, Boehringer Ingelheim), DCM (dichloromethane), PVA (poly(vinyl alcohol), Mw 13-23 000, Aldrich), Span 85 (ICI) and Tween 80 (Merck-Schuchardt) were used as purchased. The water was of ELGA quality (18.2 MΩ).

Methods: 400 µl of a 2% (w/w) NOG solution (10 mM, pH8 TRIS buffer), with the antigen, was dispersed in 1500 µl of a DCM solution, containing 3% (w/w) PLGA and 0.4% (w/w) Span™ 85/Tween™ 80 (ratio: 80/20 by weight), by probe sonication at 65 W output for 5 min. The formed $W_1/O$ emulsion was further dispersed in 56 g 10% (w/w) PVA (aq) by homogenization at 5 000 rpm for 5 min. The formation of double emulsion droplets was confirmed by light microscopy. The $(W_1/O)/W_2$ double emulsion was stirred overnight to allow the DCM to evaporate.

The volume average size of the particles was determined to 4µm by laser diffraction measurements.

EXAMPLE 7

PLGA particles incorporated with the HpaA protein were produced to an average diameter of 150 nm according to the volume size distribution, which is well suited to gastric mucosal delivery.

Materials & Methods

Materials: PL(D,L)GA (poly D,L-lactide-co-glycolide, 50:50, Mw 14400, RESOMER™ 502, Boehringer Ingelheim), DCM (dichloromethane), PVA (poly(vinyl alcohol), Mw 13-23 000, Aldrich), Tween™ 80 (Merck), Span™ 85 (Speciality Chemicals) and Laemmli sample buffer were used as purchased. The water was of ELGA quality (18.2 MΩ).

Methods: 200 µl of a 2% (w/w) NOG solution (10 mM, pH8 TRIS buffer), with the antigen, was dispersed in 800 µl of a DCM solution, containing 3% (w/w) PLGA and 0.4% (w/w) Span™ 85/Tween™ 80 (ratio: 80/20 by weight), by probe sonication at 65 W output for 10 min. The formed $W_1/O$ emulsion was further dispersed in 10 ml 10% (w/w) PVA (aq) by sonication at 65 w for 10 min. The formation of double emulsion droplets was confirmed by light microscopy. The $(W_1/O)/W_2$ double emulsion was stirred overnight to allow the DCM to evaporate. The particles were collected by centrifugation and washed with water to remove the PVA.

The volume average size of the particles was determined to 130 nm/480 nm by laser diffraction measurements. The degree of protein antigen incorporation with the PLGA particles was determined by SDS-PAGE to be 44% of the protein that was initially added.

EXAMPLE 8

PLGA particles incorporated with the HpaA protein were produced to an average diameter of approximately 13 µm according to the volume size distribution, which is well suited to gastric mucosal delivery.

Materials & Methods

Materials: PL(D,L)GA (poly D,L-lactic-co-glycolic acid, 50:50, Mw 14400, RESOMER™ 502, Boehringer Ingelheim), DCM (dichloromethane), PGPR (polyglycerol polyricinoleate, Danisco), PVA (poly(vinyl alcohol), Mw 13-23000, Aldrich), NOG (n-Octyl-glucopyranoside, SIGMA), TRIS buffer salts and Laemmli sample buffer were used as purchased. The water was of ELGA quality (18.2 MΩ).

Methods: 950 µl of an aqueous solution (10 mM TRIS buffer, pH8) containing 2% (w/w) NOG and the antigen was dispersed in 1.74 g DCM solution containing 1.8% (w/w) PGPR and 10% PLGA (w/w) by high-shear mixing at 20000 rpm for 3 min. The so-obtained $W_1/O$ emulsion was further dispersed in 50 g 10% (w/w) PVA (aq.) by high-shear mixing at 6000 rpm for 5 min. The formation of double emulsion droplets was confirmed by light microscopy. The $(W_1/O)/$ W$_2$ double emulsion was stirred overnight in an open beaker to allow the DCM to evaporate. The particles were collected by centrifugation and washed with water to remove the PVA.

The average diameter of the particles was determined to 12.6 µm by laser diffraction measurements. The protein antigen content in the dry PLGA particles was determined by SDS-PAGE to be 0.2% (w/w), which corresponds to an encapsulation degree of 44% of the protein that was initially added.

EXAMPLE 9

PLGA particles incorporated with the HpaA protein were produced to an average diameter of 9 µm according to the volume size distribution, which is well suited to gastric mucosal delivery.

Materials & Methods

Materials: PL(D,L)GA (poly D,L-lactic-co-glycolic acid, 50:50, Mw 6000, RESOMER™ 502 H, Boehringer Ingelheim), DCM (dichloromethane), PVP (poly(vinyl pyrrolidone) 5 Mw 10 000, Aldrich), PVA (poly(vinyl alcohol), Mw 13-23000, Aldrich), NOG (n-Octyl-glucopyranoside, SIGMA), TRIS buffer salts and Laemmli sample buffer were used as purchased. The water was of ELGA quality (18.2 MΩ).

Methods: 700 µl of an aqueous solution (10 mM TRIS buffer, pH8) containing 2% (w/w) NOG and the antigen was mixed with 1200 µl 2% (w/w) PVP (aq). This solution was dispersed in 3900 µl DCM solution containing 3% PLGA (w/w) by high-shear mixing at 20000 rpm for 3 min. The so-obtained W$_1$/O emulsion was further dispersed in 141 g 10% (w/w) PVA (aq.) by high-shear mixing at 5000 rpm for 6 min. The formation of double emulsion droplets was confirmed by light microscopy. The (W$_1$/O)/W$_2$ double emulsion was stirred overnight in an open beaker to allow the DCM to evaporate. The particles were collected by centrifugation and washed with water to remove the PVA.

The volume average diameter of the particles was determined to 9.3 µm by laser diffraction measurements. The protein antigen content in the dry PLGA particles was determined by SDS-PAGE to be 0.4% (w/w), which corresponds to an encapsulation degree of 93% of the protein that was initially added.

EXAMPLE 10

PHB particles incorporated with the HpaA protein were produced to an average diameter of 3 µm according to the volume size distribution, which is well suited to gastric mucosal delivery.

Materials & Methods

Materials: PHB (poly(3-hydroxybutyrate), Mw 63 500, Astra Tech), DCM (dichloromethane), PVP poly(vinyl pyrrolidone) Mw 10 000, Aldrich), PVA (poly(vinyl alcohol), Mw 13-23000, Aldrich), NOG (n-Octyl-glucopyranoside, SIGMA), TRIS buffer salts and Laemmli sample buffer were used as purchased. The water was of ELGA quality (18.2 MΩ).

Methods: 950 µl of an aqueous solution (10 mM TRIS buffer, pH8) containing 2% (w/w) NOG and the antigen was mixed with 1050 µl 2% (w/w) PVP (aq). This solution was dispersed in 3900 µl DCM solution containing 3% PHB (w/w) by high-shear mixing at 20000 rpm for 3 min. The so-obtained W$_1$/O emulsion was further dispersed in 141 g 10% (w/w) PVA (aq.) by high-shear mixing at 6000 rpm for 3 min. The formation of double emulsion droplets was confirmed by light microscopy. The (W$_1$/O)/W$_2$ double emulsion was stirred overnight in an open beaker to allow the DCM to evaporate. The particles were collected by centrifugation and washed with water to remove the PVA.

The volume average diameter of the particles was determined to 3.2 µm by laser diffraction measurements. The protein antigen content in the PHB particle suspension was determined by SDS-PAGE. The overall protein yield was determined to 34%.

B: Fluid Gas Techniques

EXAMPLE 11

Poly(3-hydroxybutyrate) (PHB) particles incorporated with the HpaA protein were produced.

General Technique

Particles were prepared in a SEDS apparatus (Bradford Particle Design, Bradford, UK) from a stabilised W/O emulsion containing the water insoluble protein antigen.

The emulsion and the anti-solvent (CO$_2$) were introduced in a coaxial nozzle, which is located inside a pressure vessel which is was located in an oven. Under controlled pressure and temperature conditions, the anti-solvent extracts the organic solvent from O phase of the formed emulsion droplets. The concentration of the matrix polymer in the droplets is thereby increased, leading to rapid particle formation. The particles were collected in a vessel, while the anti-solvent and the extracted organic solvent emerged through a back pressure regulator.

The nozzle used was a three component nozzle connected, either in a sandwich mode or in a two-solutions mode, with an opening of 0.2 mm in diameter. In the sandwich mode, the supercritical fluid passes through the innermost and the outermost passage, while the emulsion passes through the intermediate passage. In the two solution mode, the emulsion and a modifier, eg ethanol, are mixed just before contact with the fluid gas. (The modifier increases the solubility of water in the fluid gas in order to enhance water extraction.) The fluid gas passes through the outer passage, the modifier through the intermediate passage and the emulsion through the inner passage.

Materials & Methods

Materials: Poly(3-hydroxybutyrate) (PB, Astra Tech, Sweden, molecular weight (MW) 63 500 g/mol), n-Octyl-β-D-glucopyranoside (NOG), poly(vinylpyrrolidone) (PVP, Aldrich, Germany, MW 10 000 g/mol), AOT (sodium 1,4-bis (2-ethythexyl) sulphosuccinate, SIGMA. Methylene chloride (99.5%) was used as organic solvent and carbon dioxide as a supercritical fluid Ethanol (99.5%) was used as a modifier in supercritical processing.

Method: PHB was dissolved in methylene chloride at 2 bar, 90° C. Equal volumes of 2% (w/w) PVP (aq) and HpaA stock solution [1.11 mg/ml HpaA in TRIS-HCl buffer (10 mM, pH 8) and 2% (w/w) NOG], were mixed. This mixture (3.8 ml) was injected (during homogenisation at 20000 rpm) to 15.2 ml methylene chloride containing 1% (w/w) PHB and 0.4% (w/w) AOT in a 25 ml Kinematica dispersion vessel. The total homogenisation time was 3 minutes. The homogeniser used was a Polytron PT3100, Rotor PT-DA 3012/2 (Kinematica AG, Switzerland). All procedures were performed under ambient conditions.

Two runs were made with this stabilised W/O emulsion with different running conditions in the SEDS apparatus.

The run MPP63 was done by using a three-component nozzle in the two solution mode by using ethanol (flow rate 0.5 ml/min) as a modifier. In MPP64 the sandwich mode was used (Table 2).

TABLE 2

SEDS processing of emulsion

| Batch | Modifier | P (bar) | T (° C.) | Flow rate $CO_2$ (ml/min) | Flow rate emulsion (ml/min) |
|---|---|---|---|---|---|
| MPP63 | ethanol | 180 | 50 | 26 | 0.1 |
| MPP64 | — | 240 | 35 | 26 | 0.1 |

According to SEM graphs, the particle size was 1–3 μm for both trials (MPP63 and MPP64).

Theoretical composition of particles should be 55.8% (w/w) PHB, 43.5% (w/w) surfactants and 0.6% (w/w) HpaA. The analysis of the amount of HpaA gave a result of 0.4% HpaA of the total weight of the particles for both MPP63 and MPP64.

In Vivo Testing of Vaccine Delivery Systems According to the Invention

An in vivo rat model was used for screening of antibody levels in response to duodenally administered antigen delivery systems according to the preferred embodiment of the invention. This model is based on the use of Sprague-Dawley rats equipped with a chronic duodenal fistula for administration of delivery systems. IgG2a and IgA levels are investigated in blood and mucus samples respectively.

Material and Methods

A. Operation of Rats: Insertion of a Chronic Duodenal Fistula.

A fistula made of Plexiglas is inserted into the duodenum to enable administration of drugs intraduodenaly. Anaesthesia: Ketamin (Ketalar® 50 mg/ml)+Xylazin (Rompun® 20 mg/ml) mixed 8+1. There was given 0,2 ml/kg body weight ip.

Procedure: Shave and disinfect the abdomen. Make a 2–3 cm long midline incision. Make a pouch-suture with a non absorbable material (e.g. Ticron 5-0 or 4-0) about 0.5–1 cm from the pylorus in the duodenum. Make a hole in the duodenum with a 18Gx1" cannula and widen it with a small pair of tweezers. Put the cannula in the hole and tighten the suture so that it fits in with the narrow part of the fistula. Flush the fistula with physiological saline to make sure that it does not leak and to clear the fistula from blood. Make an incision laterodorsally 2 cm from the midline on the right-hand side about 1.5 cm caudal the last rib. Let the incision go through the skin and the abdominal wall. Loosen the skin around the incision. Put the fistula through the incision and suture the "wings" from the fistula to the abdominal wall with a non absorbable material (e.g. Ticron 5-0 or 4-0). Suture the midline with a absorbable material (e.g. Dexon 4-0) and the skin with non absorbable material (e.g. Dermalon 4-0). Put the cap on the fistula. Give about 10 ml fluids (e.g. Rehydrex with Glucose 25 mg/ml) subcutaneously.

B. Administration of Delivery Systems.

Upon administration the rats are put into Bollman-cages (a procedure for which rats are trained during a week following operation and prior to administration). The cap from the fistula is unscrewed and replaced with a catheter. A delivery system is administered with a syringe and a blunt cannula which exactly fits with the catheter. Close the catheter with forceps, withdraw the first syringe and put a new syringe with physiological saline onto the catheter, open the forceps and flush the rest content of the drug into the duodenum. Close the catheter with the forceps again and withdraw the syringe. Leave the catheter closed for about 5 minutes before the catheter is removed and the cap is put on the fistula C. Sampling of Blood and Mucus.

Measurements of antibody production were made following duodenal administration of antigen, delivery system including antigen, antigen+adjuvant or delivery system (including antigen)+adjuvant. The rats are administered once weekly and are terminated 10 weeks after the last immunisation. Upon termination samples are taken and evaluated. Every two weeks after the last immunisation blood-samples are collected and evaluated.

D. Antibody Analysis

Specific antibodies against the antigen are determined by ELISA as follows:

Microtiter plates are coated with the antigen (2 μg/ml in PBS) over night at 4° C. After washing three times with PBS-0.5% Tween™ 20, the wells are blocked with 2.5% non-fat dry milk in PBS for 1 hour at room temperature. Triplicate wells are incubated with serial sample dilutions for 1 h at room temperature. For IgG2a quantification, a standard serum is applied in serial dilutions to each plate. After washing, the wells are incubated with biotinylated mouse-anti rat IgG2a (serum) or IgA (mucus), diluted 1:1000 respectively for 1 h at room temperature. This is followed by 1 h incubation at room temperature with avidin-alkaline phosphatase, diluted 1:500. The plates are developed by using alkaline phosphatase substrate (pNPP) and colour development is recorded at 405 nm after 20 minutes.

In Vivo Trials and Results

A sample of rats was used in in vivo trials to determine the capacity for polymer particles according to Example 1 to act as a mucosal vaccine delivery system. Rats were immunised with either (i) 100 μg HpaA+25 μg Cholera toxin(CT) (sample size: 4 rats); or (ii) the polymer particle delivery system of Example 1 (HpaA/PLG) containing 100 μg HpaA (sample size: 6 rats). Three immunisations were carried out for each rat (one per week), and sampling was carried out 7 weeks after the third immunisation. Negative controls were obtained by sampling prior to the first immunisation of the HpaA+Cholera toxin group.

The combination of protein (HpaA)+the mucosal adjuvant CT was used as a positive control.

The results are presented in FIGS. 5 and 6. It can be seen from the results in FIG. 6 that the polymer particles according to the present invention (HpaA/PLG in the figure) clearly deliver the antigen such that an anti-HpaA mucosal immune response is stimulated in the animals. This demonstrates the utility of the polymer particles according to the present invention as a delivery system for a vaccine, in the present trials a vaccine for treating and/or preventing Helicobacter infection. In particular, it is noteable that in FIG. 6 the result with the polymer particles according to the present invention is comparable to the result obtained with the positive control of HpaA+CT.

What is claimed is:

1. A method for producing an antigen delivery system comprising a plurality of polymer particles, wherein a water-insoluble protein antigen is incorporated with the polymer particles, the polymer particles comprising a matrix polymer which comprises one or more homo- and/or copolymers, wherein the method comprises:

(a) mixing an aqueous phase (W) comprising the water-insoluble protein and one or more hydrophilic surfactants at a concentration of 0.1 to 100 times the critical micelle concentration thereof with an organic phase (O) that comprises the matrix polymer in an organic solvent, which solvent does not denature the protein antigen and wherein O is immiscible with W, to produce a W/O emulsion, wherein either W or O or both further comprise one or more stabilizing agents added prior to mixing to stabilize the W/O emulsion in the presence of the solubilizing agent(s) and promote the incorporation of the water-insoluble protein within the polymer particles during step (b); and (b) forming droplets of said W/O emulsion by dispersing the emulsion in a fluid medium, and removing said solvent from the O phase of the W/O emulsion droplets to thereby form the polymer particles incorporating the water-insoluble protein antigen.

2. The method of claim 1, wherein more than one stabilizing agent is included in the W/O emulsion.

3. The method of claim 2, wherein one of the stabilizing agents is a sorbitan fatty acid ester.

4. The method of claim 2, wherein the stabilizing agents comprise poly (vinyl pyrrolidone) and sodium 1,4-bis(2-ethylhexyl) sulphosuccinate.

5. The method of claim 1 or 2, wherein the one or more stabilizing agents is/are selected from the group consisting of polymers, polar lipids, and hydrophobic surfactants.

6. The method of claim 5, wherein the one or more stabilizing agents is/are a polymer selected from the group consisting of poly(vinyl pyrrolidone), poly(vinyl alcohol), polysaccharides, polyethyleneoxide and water-soluble proteins.

7. The method of claim 5, wherein the one or more stabilizing agents is/are a polar lipid selected from the group consisting of cholesterol, phosphatidylcholine, phosphatidylethanolamine, phosphatidylglycerol, glycolipids and phosphatidic acid.

8. The method of claim 5, wherein the one or more stabilizing agents is/are a non-ionic, hydrophobic surfactant selected from the group consisting of a sorbitan fatty acid ester, hydrophobic polyoxyethylene alkyl ether, sucrose ester, alkyl-glucopyranoside, polyglycerol polyricinoleate and block-copolymers of ethylene oxide with propyleneoxide and/or lactic acid.

9. The method of claim 5, wherein the one or more stabilizing agents is/are an anionic, hydrophobic surfactant selected from the group consisting of an alkylsulphate salt, a dialkylsulphosuccinate salt, an alkylbenzene sulphonate salt and a fatty acid salt.

10. The method of claim 5, wherein the one or more stabilizing agents is/are a cationic, hydrophobic surfactant selected from the group consisting of an alkyltrimethylammonium salt and a dialkyldimethylammonium salt.

11. The method of claim 1, wherein the aqueous phase comprises more than one solubilizing agent.

12. The method of claim 1, wherein the hydrophilic surfactant is a non-ionic surfactant selected from the group consisting of alkyl-glucopyranosides, alkyl-thioglucopyranosides, alkyl-maltosides, alkoyl-methyl glucamides, glucamides, polyoxyethylene alcohols, polyoxyethylene alkyl phenols, emulphogens, polyoxyethylene sorbitol esters, polyoxyethylene fatty acid esters, hydrophilic polyoxyethylene alkyl ethers and digitonin.

13. The method of claim 1, wherein the hydrophilic surfactant is an anionic surfactant selected from the group consisting of cholates, alkylsulphonates, deoxycholates, alkylsulphates, oligooxyethylene dodecyl ether sulphates and sodium dodecylsarcosinate.

14. The method of claim 1, wherein the hydrophilic surfactant is a cationic surfactant selected from the group consisting of alkylpyridinium salts and alkyltrimethylammonium salts.

15. The method of claim 1, wherein the hydrophilic surfactant is a zwitterionic surfactant selected from the group consisting of 3-1-propanesulphonate (CHAPS), 3-[(3-cholamidopropyl)-dimethylammonio]-2-hydroxy-1-propanesulphonate (CHAPSO), N,N-bis-cholamide (BIGCHAP), N,N-bis-deoxycholamide (deoxy BIGCHAP), lyso phosphatidylcholine, alkylbetaines and sulphobetaines.

16. The method of claim 1 which includes a Double Emulsion (W/O/X) Solvent Evaporation Technique wherein the fluid medium in which the stabilized W/O emulsion is dispersed in step (b) is a liquid phase (X) which is immiscible with the O phase, said method producing a W/O/X double emulsion comprising W/O droplets from which the solvent is evaporated.

17. The method of claim 1 which includes a Double Emulsion (W/O/X) Solvent Extraction Technique wherein the fluid medium in which the stabilized W/O emulsion is dispersed in step (b) is a liquid phase (X) which is immiscible with the O phase, said method producing a W/O/X double emulsion comprising W/O droplets, and wherein the removal of the organic solvent from the O phase of the droplets is achieved through extraction by the X phase.

18. The method of claim 16 or 17, wherein the X phase comprises a stabilizing agent.

19. The method of claim 18, wherein the one or more stabilizing agents is/are selected from group consisting of polymers, polar lipids, and hydrophobic surfactants.

20. The method of claim 18, wherein the one or more stabilizing agents is/are a polymer selected from the group consisting of poly(vinyl pyrrolidone), poly(vinyl alcohol), polysaccharides, polyethyleneoxide and water soluble proteins.

21. The method of claim 18, wherein the one or more stabilizing agents is/are a polar lipid selected from the group consisting of cholesterol, phosphatidylcholine, phosphatidylethanolamine, phosphatidylglycerol, glycolipids and phosphatidic acid.

22. The method of claim 18, wherein the one or more stabilizing agents is/are a non-ionic, hydrophobic surfactant selected from the group consisting of sorbitan fatty acid ester, hydrophobic polyoxyethylene alkyl ether, sucrose ester, alkyl-glucopyranoside, polyglycerol polyricinoleate and block-copolymers of ethylene oxide with propyleneoxide and/or lactic acid.

23. The method of claim 18, wherein the one or more stabilizing agents is/are an anionic, hydrophobic surfactant selected from an alkylsulphate salt, dialkylsulphosuccinate salt, alkylbenzene sulphonate salt and a fatty acid salt.

24. The method of claim 18, wherein the one or more stabilizing agents is/are a cationic, hydrophobic surfactant selected from the group consisting of an alkyltrimethylammonium salt and a dialkyldimethylammonium salt.

25. The method of claim 1, wherein the dispersal of the stabilized W/O emulsion in a fluid medium during polymer formulation in step (b) is schieved with a spray drying technique, wherein the stabilized W/O emulsion is dispersed in a gaseous medium to form a spray of W/O emulsion droplets from which said solvent evaporates.

26. The method of claim 1, wherein the dispersal of the stabilized W/O emulsion in a fluid medium during polymer particle formulation in step (b) is achieved with a fluid gas technique.

27. The method of claim 26, wherein the fluid gas technique is selected From the group consisting of gas anti-solvent precipitation (GAS), solution enhanced dispersion by supercritical fluid (SEDS), precipitation with compressed anti-solvents (PCA), supercritical anti-solvent (SAS) and aerosol solvent extraction system (ASES).

28. The method of claim 1, wherein the protein antigen is a Helicobacter protein or Helicobacter protein fragment.

29. The method of claim 28, wherein the Helicobacter protein or Helicobacter protein fragment is from *Helicobacter pylori*.

30. The method of claim 28 or 29, wherein said Helicobacter protein is a protein expressed on the surface of Helicobacter.

31. The method of claim 30, wherein the protein part of the lipidated HpaA protein has an amino acid sequence that is identical to, or substantially similar to, positions 28 to 260 of SEQ ID NO. 2 or 4.

32. The method of claim 30, wherein the Helicobacter protein is a lipidated form of *Helicobacter pylori* adhesion antigen (HpaA).

33. The method of claim 32, wherein the protein is a fully lipidated form of HpaA.

34. The method of claim 1, wherein the matrix polymer is selected from one or more of the group consisting of polyesters, polyanhydrides, polyorthoesters, polycarbonates, polyamides, poly(amino acids), polyacetals, polycyanoacrylates, polyacrylates, biodegradable polyurethanes, non-erodible polyurethanes, polymers of ethylene-vinyl acetate, acyl substituted cellulose acetates, polysaccharides, polystyrenes, polyvinyl chloride, polyvinyl fluoride, poly(vinyl imidazole), chlorosulphonated polyolefins, polyethylene oxide, polyethers and polyoxalates.

35. The method of claim 1, wherein the matrix polymer is a polyester homopolymer selected from the group consisting of polylactic acid, polyglycolic acid, polyhydroxybutyrate, poly(alpha hydroxyacids) and polycaprolactone.

36. The method of claim 1, wherein the matrix polymer is a polyester co-polymer selected from the group consisting of poly(lactide-co-glycolide), poly(lactic-co-glycolic acid), poly(hydroxybutyrate-hydroxyvalerate) and poly(lactide-co-caprolactone).

37. The method of claim 36, wherein the matrix polymer is poly(D,L-lactide-co-glycolide).

38. The method according to claim 1 wherein the organic solvent in the organic phase (O) is selected from the group consisting of methylene chloride, chloroform and ethyl acetate.

39. The method of claim 1, wherein in step (a) the W phase is mixed with the O phase in a ratio by volume of 1:10 to 1:1.

40. An antigen delivery system produced by the method of claim 1, wherein the one or more stabilizing agents is/are a polymer selected from the group consisting of poly(vinyl pyrrolidone), poly(vinyl alcohol), polysaccharides, polyethyleneoxide and water soluble proteins, and wherein the method includes a Double Emulsion (W/O/X) Solvent Evaporation Technique wherein the fluid medium in which the stabilized W/O emulsion is dispersed in step (b) is a liquid phase (X) which is immiscible with the O phase, said method producing a W/O/X double emulsion comprising W/O droplets from which the solvent is evaporated.

41. The antigen delivery system of claim 40, wherein the matrix polymer is selected from one or more of the group consisting of polyesters, polyanhydrides, polyorthoesters, polycarbonates, polyamides, poly(amino acids), polyacetals, polycyanoacrylates, polyacrylates, biodegradable polyurethanes, non-erodible polyurethanes, polymers of ethylene-vinyl acetate, acyl substituted cellulose acetates, polysaccharides, polystyrenes, polyvinyl chloride, polyvinyl fluoride, poly(vinyl imidazole), chlorosulphonated polyolefins, polyethylene oxide, polyethers and polyoxalates.

42. The antigen delivery system of claim 41, wherein the polymer is a polyester homopolymer selected from the group consisting of polylactic acid, polyglycolic acid, polyhydroxybutyrate, poly(alpha hydroxyacids) and polycaprolactone.

43. The antigen delivery system of claim 41, wherein the matrix polymer is a polyester co-polymer selected from the group consisting of poly(lactide-co-glycolide), poly(lactic-co-glycolic acid), poly(hydroxybutyrate-hydroxyvalerate) and poly(lactide-co-caprolactone).

44. The antigen delivery system of claim 43, wherein the matrix polymer is poly(D,L-lactide-co-glycolide).

45. The antigen delivery system of any one of claims 40 and 41–44 wherein the polymer particles have an average diameter of 0.05–20 μm according to the volume size distribution.

46. An immunogenic composition comprising the delivery system of claim 45.

47. A method for inducing an immune response directed toward preventing or reducing the risk of Helicobacter infection in a mammalian host, comprising administering to the mammalian host an effective amount of the composition according to claim 46 wherein the water-insoluble protein antigen is a Helicobacter antigen.

48. The method according to claim 47 wherein the protein antigen is a lipidated form of *Helicobacter pylori* adhesion antigen (HpaA).

49. The method according to claim 48 wherein the protein part of the lipidated antigen has an amino acid sequence that is identical to, or substantially similar to, positions 28 to 260 of SEQ ID NO. 2 or 4.

50. A method for inducing an immune response directed against existing Helicobacter infection in a mammalian host comprising administering to the mammalian host an effective amount of the composition according to claim 46 wherein the water-insoluble protein antigen is a Helicobacter antigen.

51. The method according to claim 50 wherein the protein antigen is a lipidated form of *Helicobacter pylori* adhesion antigen (HpaA).

52. The method according to claim 51 wherein the protein part of the lipidated antigen has an amino acid sequence that is identical to, or substantially similar to, positions 28 to 260 of SEQ ID NO. 2 or 4.

53. An immunogenic composition comprising the delivery system of any one of claims 40 and 41–44.

54. A method for inducing an immune response directed toward preventing or reducing the risk of Helicobacter infection in a mammalian host, comprising administering to the mammalian host an effective amount of the composition according to claim 53 wherein the water-insoluble protein antigen is a Helicobacter antigen.

55. The method according to claim 54 wherein the protein antigen is a lipidated form of *Helicobacter pylori* adhesion antigen (HpaA).

56. The method according to claim 55 wherein the protein part of the lipidated antigen has an amino aced sequence that is identical to, or substantially similar to, positions 28 to 260 of SEQ ID NO. 2 or 4.

57. A method for inducing an immune response directed against existing Helicobacter infection in a mammalian host, comprising administering to the mammalian host an effective amount of the composition according to claim 53, wherein the water-insoluble protein antigen is a Helicobacter antigen.

58. The method according to claim 57 wherein the protein antigen is a lipidated form of *Helicobacter pylori* adhesion antigen (HpaA).

59. The method according to claim 58 wherein the protein part of the lipidated antigen has an amino acid sequence that is identical to, or substantially similar to, positions 28 to 260 of SEQ ID NO. 2 or 4.

60. The composition according to claim 53 wherein the protein antigen is a Helicobacter antigen.

61. The composition according to claim 60 wherein the protein antigen is a lipidated form of *Helicobacter pylori* adhesion antigen (HpaA).

62. The composition according to claim 61 wherein the protein part of the lipidated antigen has an amino acid sequence that is identical to, or substantially similar to, positions 28 to 260 of SEQ ID NO. 2 or 4.

63. The composition according to claim 46 wherein the protein antigen is a Helicobacter antigen.

64. The composition according to claim 63 wherein the protein antigen is a lipidated form of *Helicobacter pylori* adhesion antigen (HpaA).

65. The composition according to claim 64 wherein the protein part of the lipidated antigen has an amino acid sequence that is identical to, or substantially similar to, positions 28 to 260 of SEQ ID NO. 2 or 4.

* * * * *

UNITED STATES PATENT AND TRADEMARK OFFICE
CERTIFICATE OF CORRECTION

PATENT NO. : 6,838,089 B1
DATED : January 4, 2005
INVENTOR(S) : Hans Carlsson et al.

It is certified that error appears in the above-identified patent and that said Letters Patent is hereby corrected as shown below:

Column 45,
Line 54, "schieved" bshould read -- achieved --.

Column 46,
Line 44, "volume of 1:10" should read -- volume of 1:100 --.

Column 48,
Line 11, "aced" should read -- acid --.

Signed and Sealed this

Twelfth Day of April, 2005

JON W. DUDAS
*Director of the United States Patent and Trademark Office*